(12) United States Patent
Crawford et al.

(10) Patent No.: US 12,333,652 B2
(45) Date of Patent: Jun. 17, 2025

(54) METHOD FOR GENERATING A 3D PRINTABLE MODEL OF A PATIENT SPECIFIC ANATOMY

(71) Applicant: Axial Medical Printing Limited, Belfast (GB)

(72) Inventors: Daniel Crawford, Belfast (GB); Catherine Coomber, Belfast (GB); Niall Haslam, Belfast (GB)

(73) Assignee: Axial Medical Printing Limited, Belfast (GB)

( * ) Notice: Subject to any disclaimer, the term of this patent is extended or adjusted under 35 U.S.C. 154(b) by 0 days.

(21) Appl. No.: 18/751,032

(22) Filed: Jun. 21, 2024

(65) Prior Publication Data

US 2024/0346768 A1 Oct. 17, 2024

Related U.S. Application Data

(63) Continuation of application No. 17/929,702, filed on Sep. 4, 2022, now Pat. No. 12,020,375, which is a (Continued)

(30) Foreign Application Priority Data

Jan. 11, 2019 (GB) ...................... 1900437

(51) Int. Cl.
*G06T 15/00* (2011.01)
*G06N 3/08* (2023.01)
(Continued)

(52) U.S. Cl.
CPC ............... *G06T 17/20* (2013.01); *G06N 3/08* (2013.01); *G06N 20/20* (2019.01); *G06T 7/0012* (2013.01);
(Continued)

(58) Field of Classification Search
CPC ......... G06T 7/0012; G06T 17/00; G06T 7/11; G06T 17/20; G06T 19/00;
(Continued)

(56) References Cited

U.S. PATENT DOCUMENTS

| 5,859,891 A | 1/1999 | Hibbard |
| 9,437,119 B1 | 9/2016 | Bernal |
| (Continued) | | |

FOREIGN PATENT DOCUMENTS

| CN | 105608728 A | 5/2016 |
| CN | 106373168 A | 2/2017 |
| (Continued) | | |

OTHER PUBLICATIONS

U.S. Appl. No. 18/407,286, filed Jan. 8, 2024.
(Continued)

*Primary Examiner* — Phu K Nguyen
(74) *Attorney, Agent, or Firm* — Greenberg Traurig, LLP; Christopher C. Bolten; Albert K. Heng

(57) ABSTRACT

A computer implemented method for generating a 3D printable model of a patient specific anatomic feature from 2D medical images is provided. A 3D image is automatically generated from a set of 2D medical images. A machine learning based image segmentation technique is used to segment the generated 3D image. A 3D printable model of the patient specific anatomic feature is created from the segmented 3D image.

30 Claims, 16 Drawing Sheets

Related U.S. Application Data continuation of application No. 17/372,087, filed on Jul. 9, 2021, now Pat. No. 11,436,801, which is a continuation of application No. PCT/GB2020/050063, filed on Jan. 13, 2020.

(51) Int. Cl.

| | | |
|---|---|---|
| *G06N 20/20* | (2019.01) | |
| *G06T 7/00* | (2017.01) | |
| *G06T 7/11* | (2017.01) | |
| *G06T 17/20* | (2006.01) | |
| *G16H 30/40* | (2018.01) | |
| *G16H 50/50* | (2018.01) | |

(52) U.S. Cl.
CPC ............... *G06T 7/11* (2017.01); *G16H 30/40* (2018.01); *G16H 50/50* (2018.01); *G06T 2207/20081* (2013.01); *G06T 2207/20084* (2013.01); *G06T 2207/30048* (2013.01); *G06T 2207/30104* (2013.01); *G06T 2210/41* (2013.01)

(58) Field of Classification Search
CPC . G06T 2207/30048; G06T 2207/30104; G06T 2210/41; G06T 2207/20084; G06T 2207/20081; G16H 50/50; G16H 30/40; G06N 3/08; G06N 20/20
USPC ........................................................ 345/418
See application file for complete search history.

(56) References Cited

U.S. PATENT DOCUMENTS

| | | | |
|---|---|---|---|
| 9,646,411 | B2 | 5/2017 | Lee |
| 10,032,281 | B1 | 7/2018 | Ghesu et al. |
| 10,409,235 | B2 | 9/2019 | Zhou et al. |
| 10,946,586 | B2 | 3/2021 | Casey et al. |
| 10,981,680 | B2 | 4/2021 | Colson et al. |
| 11,010,800 | B2 | 5/2021 | Norman |
| 11,059,228 | B2 | 7/2021 | Elber et al. |
| 11,138,790 | B2 | 10/2021 | Haslam et al. |
| 11,288,865 | B2 | 3/2022 | Haslam et al. |
| 11,436,801 | B2 | 9/2022 | Haslam et al. |
| 11,497,557 | B2 | 11/2022 | Haslam et al. |
| 11,551,420 | B2 | 1/2023 | Haslam et al. |
| 11,626,212 | B2 | 4/2023 | Crawford et al. |
| 11,715,210 | B2 | 8/2023 | Haslam et al. |
| 11,869,670 | B2 | 1/2024 | Crawford et al. |
| 11,922,631 | B2 | 3/2024 | Haslam et al. |
| 12,020,375 | B2 | 6/2024 | Haslam et al. |
| 2009/0316975 | A1 | 12/2009 | Kunz et al. |
| 2010/0156904 | A1 | 6/2010 | Hartung |
| 2011/0038516 | A1 | 2/2011 | Koehler et al. |
| 2011/0218428 | A1 | 9/2011 | Westmoreland et al. |
| 2012/0059252 | A1 | 3/2012 | Li et al. |
| 2012/0224755 | A1 | 9/2012 | Wu |
| 2013/0002646 | A1 | 1/2013 | Lin et al. |
| 2014/0328529 | A1 | 11/2014 | Koceski et al. |
| 2014/0361453 | A1 | 12/2014 | Triantafyllou |
| 2015/0089337 | A1 | 3/2015 | Grady et al. |
| 2015/0169985 | A1 | 6/2015 | Burger et al. |
| 2015/0342537 | A1 | 12/2015 | Taylor et al. |
| 2016/0086078 | A1 | 3/2016 | Ji et al. |
| 2016/0110517 | A1* | 4/2016 | Taylor .................... A61B 5/055 |
| 2016/0300350 | A1 | 10/2016 | Choi et al. |
| 2017/0007129 | A1 | 1/2017 | Kaib et al. |
| 2017/0228505 | A1 | 8/2017 | Allen et al. |
| 2017/0245821 | A1* | 8/2017 | Itu ........................ A61B 8/5223 |
| 2017/0329930 | A1 | 11/2017 | Fonte et al. |
| 2018/0028265 | A1 | 2/2018 | Azevedo et al. |
| 2018/0092699 | A1* | 4/2018 | Finley ................... A61B 34/20 |
| 2018/0165867 | A1 | 6/2018 | Kuhn et al. |
| 2018/0276815 | A1 | 9/2018 | Xu et al. |
| 2018/0365835 | A1 | 12/2018 | Yan et al. |
| 2019/0053855 | A1 | 2/2019 | Siemionow et al. |
| 2019/0105009 | A1 | 4/2019 | Siemionow et al. |
| 2019/0108635 | A1 | 4/2019 | Hibbard et al. |
| 2019/0205606 | A1 | 7/2019 | Zhou et al. |
| 2019/0251694 | A1 | 8/2019 | Han et al. |
| 2019/0392942 | A1 | 12/2019 | Sorenson et al. |
| 2020/0074637 | A1 | 3/2020 | Wong |
| 2020/0367970 | A1 | 11/2020 | Qiu et al. |
| 2020/0402647 | A1 | 12/2020 | Domracheva et al. |
| 2021/0068714 | A1 | 3/2021 | Crowley et al. |
| 2021/0074425 | A1 | 3/2021 | Carter et al. |
| 2021/0097690 | A1 | 4/2021 | Mostapha et al. |
| 2021/0110605 | A1 | 4/2021 | Haslam et al. |
| 2021/0335041 | A1 | 10/2021 | Haslam et al. |
| 2023/0281842 | A1 | 9/2023 | Ribeiro et al. |
| 2024/0005504 | A1 | 1/2024 | Ribeiro et al. |

FOREIGN PATENT DOCUMENTS

| | | | |
|---|---|---|---|
| EP | 3020537 | A1 | 5/2016 |
| WO | WO-2016161198 | A1 | 10/2016 |
| WO | WO-2018069736 | A1 | 4/2018 |
| WO | WO-2018222779 | A1 | 12/2018 |
| WO | WO-2020144483 | A1 | 7/2020 |
| WO | WO-2023096516 | A1 | 6/2023 |

OTHER PUBLICATIONS

U.S. Appl. No. 18/595,213, filed Mar. 4, 2024.
Aisaeed et al., "A Novel Fast Otsu Digital Image Segmentation Method," The International Arab Journal of Information Technology, vol. 13(4):427-433 (Jul. 2016).
Baghaie, et al., An Optimization Method For Slice Interpolation of Medical Images, arXiv preprint arXiv:1402.0936 (Feb. 2014).
Boulton, et al., Lessons from the National Hip Fracture Database, Orthopaedics and Trauma, 30(2):123-127 (Apr. 2016).
Brown, et al., Using Machine Learning for Sequence-Level Automated MRI Protocol Selection in Neuroradiology, Journal of the American Medical Informatics Association, 25(5):568-71 (May 2018).
Carvalho, et al., Estimating 3D lumen centerlines of carotid arteries in free-hand acquisition ultrasound, International Journal of Computer Assisted Radiology and Surgery, 7(2):207-215 (Mar. 2012).
Cui, et al., Brain MRI Segmentation with Patch-Based CNN Approach, Proceedings of the 35th Chinese Control Conference, Jul. 27-29, 2016, pp. 7026-7031.
Dou, et al., 3D Deeply Supervised Network for Automated Segmentation of Volumetric Medical Images, Medical Image Analysis, 41:40-54 (Oct. 2017).
Geremia, et al., Spatial Decision Forests for MS Lesion Segmentation in Multi-Channel Magnetic Resonance Images, NeuroImage, 57(2):378-390 (Jul. 2011).
Heckelman, et al., "Design and validation of a semi-automatic bone segmentation algorithm from MRI to improve research efficiency," Scientific Reports, vol. 12:7825, https://doi.org/10.1038/s41598-022-11785-6 (2022).
International Search Report & Written Opinion dated Feb. 16, 2018 in Int'l PCT Patent Appl. Serial No. PCT/GB2017/053125.
International Search Report & Written Opinion dated May 12, 2022 in Int'l PCT Patent Appl. Serial No. PCT/IB2022/051216.
International Search Report & Written Opinion dated Jun. 25, 2020 in Int'l PCT Patent Appl. Serial No. PCT/GB2020/050063.
Laosai et al., Acute Leukemia Classification by Using SVM and K-Means Clustering, 2014 Proceedings of the International Electrical Engineering Congress (IEECON), pp. 1-4 (Mar. 19, 2014).
Lee, et al., Human Airway Measurement from CT Images. In Medical Imaging 2008: Computer-Aided Diagnosis, Proc. SPIE 6915:386-383 (Mar. 2008).
Litjens, et al., A Survey on Deep Learning in Medical Image Analysis, Medical Image Analysis, 42:60-88 (Dec. 2017).
Milletari, et al., V-Net: Fully Convolutional Neural networks for Volumetric Medical Image Segmentation, arXiv preprint arXiv: 1606.04797 (Jun. 2016).

(56) References Cited

OTHER PUBLICATIONS

Monteiro et al., "Conditional Random Fields as Recurrent Neural Networks for 3D Medical Imaging Segmentation," arXiv preprint arXiv:1807.07464, (Jul. 2019).
Mortensen et al., "Semantic Segmentation of Mixed Crops Using Deep Convolutional Neural Network," CIGr-AgEng Conference, pp. 26-29, (Jun. 2016).
Pinheiro et al., A new Level-Set-Based Protocol for Accurate Bone Segmentation from CT Imaging, IEEE Access, vol. 3:1894-1906 (Sep. 2015).
Richmond et al., "Mapping Stacked Decision Forests to Deep and Sparse Convolution Neural Networks for Semantic Segmentation," arXiv, pp. 1-15 (Dec. 2015).
Rogowska, et al., Overview and Fundamentals of Medical Image Segmentation, Handbook of Medical Imaging, Processing and Analysis, pp. 69-85 (Oct. 2000).
Schmauss D., et al., "Three-Dimensional Printing in Cardiac Surgery and Interventional Cardiology: A Single-Centre Experience," European Journal of Cardio-Thoracic Surgery, Aug. 26, 2014, vol. 47(6), pp. 1044-1052.
Tabrizi, et al., "Acetabular cartilage segmentation in CT arthrography based on a bone-normalized probabilistic atlas," Int J CARS, vol. 10:433-446 (2015).
Yu, et al., 3D FractalNet: Dense Volumetric Segmentation for Cardiovascular MRI Volumes, in Reconstruction, Segmentation, and Analysis of Medical Images, pp. 103-110 (Oct. 2016).
Yu, et al., 3D FractaNet: dense volumetric segmentation for cardiovascular MRI volumes. In Reconstruction, Segmentation, and Analysis of Medical Images. First International Workshops, RAMBO 2016 and HVSMR 2016. Held in Conjunction with MICCAI 2016, Athens, Greece, Oct. 17, 2016, Revised Select.
Zhou, et al., Deep convolutional neural network for segmentation of knee joint anatomy, Mag. Reson. Med., 80(6):2759-2770 (Dec. 2018).
Zhuang, J., "Laddernet: Multi-Path Networks based on U-Net for Medical Image Segmentation," arXiv:preprint arXiv:1810.07810., pp. 1-4, (Oct. 2018).

* cited by examiner

METHOD FOR GENERATING A 3D PRINTABLE MODEL OF A PATIENT SPECIFIC ANATOMY

CROSS-REFERENCE TO RELATED APPLICATIONS

This application is a continuation application of U.S. patent application Ser. No. 17/929,702, filed Sep. 4, 2022, now U.S. Pat. No. 12,020,375, which is a continuation application of U.S. patent application Ser. No. 17/372,087, filed Jul. 9, 2021, now U.S. Pat. No. 11,436,801, which is a continuation application of PCT Patent Appl. No. PCT/GB2020/050063, filed Jan. 13, 2020, which claims priority to UK Patent Appl. No. 1900437.3, filed Jan. 11, 2019, the entire contents of each of which are incorporated herein by reference.

BACKGROUND OF THE INVENTION

1. Field of the Invention

The field of the invention relates to a computer implemented method for generating a 3D printable model of a patient specific anatomy based on 2D medical images.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2. Description of the Prior Art

Creating accurate 3D printed models of specific parts of a patient's anatomy is helping to transform surgery procedures by providing insights to clinicians for preoperative planning. Benefits include for example better clinical outcomes for patients, reduced time and costs for surgery and the ability for patients to better understand a planned surgery.

However, there is still a need to provide a secure platform which would enable the ordering and delivery of 3D printed models in a timely and customisable manner. Additionally, there is also a need to provide 3D printable models providing greater insight on the patient anatomy or pathology.

SUMMARY OF THE INVENTION

There is provided a computer implemented method for generating a 3D printable model of a patient specific anatomic feature from 2D medical images, in which a 3D image is automatically generated from a set of 2D medical images, a machine learning based image segmentation technique is used to segment the generated 3D image, and a 3D printable model of the patient specific anatomic feature is created from the segmented 3D image.

Optional features in an implementation of the invention include any one or more of the following:

- The set of 2D medical images are images from the patient taken from one or a combination of the following: CT, MRI, PET and/or SPCET scanner.
- 2D medical images from multiple scanning techniques are simultaneously processed.
- The set of 2D medical images is automatically pre-processed such that important or critical features of the patient specific anatomic features are made visible within the 3D printable model.
- Pre-processing of the 2D medical images is based on the specific anatomic feature, specific pathology of the patient or any downstream application such as preoperative planning or training purpose.
- The set of 2D medical images is pre-processed to generate a new set of 2D medical images which are evenly distributed according to a predetermined orientation.
- The predetermined orientation is based on the patient specific anatomic feature, specific pathology of the patient or any downstream application such as preoperative planning or training purpose.
- The predetermined orientation and spacing between each 2D medical image within the new set of 2D medical images are determined using machine learning techniques.
- The predetermined orientation and spacing between each 2D medical image within the new set of 2D medical images are user configurable.
- A missing slice from the set of 2D medical images is automatically detected.
- A 2D image corresponding to the missing slice is generated using interpolation techniques.
- The segmentation technique is based on one or a combination of the following techniques: threshold-based, decision tree, chained decision forest and a neural network method.
- Voxel based classification technique is used in which voxel information from each axis or plane is taken into account.
- The likelihood of a voxel of the 3D image having properties similar to the patient specific anatomic feature is calculated using a logistic or probabilistic function.
- A neural network determines a weight for each axis or plane in each voxel of the 3D image.
- The segmentation technique is further improved using multi-channel training.
- Each channel represents a 2D image corresponding to a slice position within the 3D space of the 3D image.
- A channel is represented using a ground truth image.
- A 3D mesh model of the patient specific anatomic feature is generated from the segmented 3D image, and the 3D printable model is generated from the 3D mesh model.
- The 3D mesh model is further processed using finite element analysis.
- Points or areas in the 3D mesh model requiring further post processing steps are automatically detected.
- Further post processing steps include placement of a dowel or other joining structure.
- The optimal placement of a dowel or other joining structure is automatically determined.
- Parameters of the patient anatomic feature are automatically determined from the analysis of the generated 3D image, such as volume or dimensions of the anatomic feature, thicknesses of the different layers of the anatomic feature.
- Specific anatomic feature is a heart and the measured parameters include one of the following: volume of the heart, volume of blood in each chamber of the heart, thickness of the different layers of the heart wall, size of a specific vessel.
- The 3D printable model is 3D printed as a 3D physical model such that it represents a scale model of the patient specific anatomic feature such as a 1:1 scale model or a more appropriate scale model such as a reduced scale or enlarged scale model of the patient specific anatomic feature depending on the intended downstream application.

The 3D printable model is 3D printed with critical or important features of the specific anatomic feature made easily visible or accessible.

A 3D mesh is generated from the set of 2D medical images, in which the 3D mesh is a polygonal representation of the volume of the patient specific anatomic feature.

A line or spline is extracted from the 3D mesh along a direction of the patient specific anatomic feature.

A classifier is used to identify the anatomic feature from the extracted line or spline.

The method further includes the step of generating a wireframe model of the 3D mesh.

A classifier is used to identify the physical properties of the anatomic feature from the extracted line or spline.

A classifier is used to identify a pathology of the anatomic feature from the extracted line or spline.

The classifier is trained to identify a specific anatomical feature.

The classifier is trained to determine parameters of the specific anatomic feature such as its location relative to the human body, dimension or thickness.

The classifier is trained to determine a potential defect or pathology of the specific anatomic feature.

The classifier is a principle component analysis classifier.

The method further includes the step of splitting the 3D printable model into a set of 3D printable models, in which the set of 3D printable models include connective pieces, in which the location of each connective piece is automatically generated.

The 3D printable model is decided based on the patient specific anatomy and pathology.

Splitting of the 3D printable model cannot be decided only on assessing the surface of the patient specific anatomy.

A connective piece is a magnetic or metal element.

Each connective piece is located such that a set of 3D printed physical models from the set of 3D printable models can be connected to represent the patient specific anatomic feature and is prevented from being wrongfully connected.

The set of 3D printed physical models represent a scale model of the patient specific anatomic feature such as a 1:1 scale model or a more appropriate scale model such as a reduced scale or enlarged scale model of the patient specific anatomic feature depending on the intended downstream application.

Critical or important features of the specific anatomic feature are made easily visible within the set of 3D printable physical models.

Critical or important features of the specific anatomic feature are made easily accessible within the set of 3D printable physical models.

Another aspect is a 3D physical model representing a scale model of a patient specific anatomic feature that is 3D printed from the 3D printable model generated from the method steps defined above, in which the scale model is a 1:1 scale model or a more appropriate scale model such as a reduced scale or enlarged scale model of the patient specific anatomic feature depending on the intended downstream application Another aspect is a computer implemented system for generating a 3D printable model of a patient specific anatomic feature from a set of 2D medical images, the system comprising a processor for automatically generating a 3D image from the set of 2D medical images, segmenting the generated 3D image using a machine learning based image segmentation technique, and outputting a 3D printable model of the patient specific anatomic feature from the segmented 3D image.

Another aspect is a computer implemented method for printing a 3D model of a patient specific anatomic feature comprising: uploading a set of 2D medical images to a server, processing at the server the set of 2D medical images into a 3D printable model of the patient specific anatomic feature; the server transmitting instructions for printing the 3D printable model to a printer, in which a security engine validates that the 3D printable model is associated with the correct patient data, and in which an end-user located at a remote location from the printer manages the printing of the 3D printable model.

BRIEF DESCRIPTION OF THE FIGURES

Aspects of the invention will now be described, by way of example(s), with reference to the following Figures, which each show features of the invention.

DETAILED DESCRIPTION

This Detailed Description section describes one implementation of the invention, called the Axial3D system.

Figure 1:
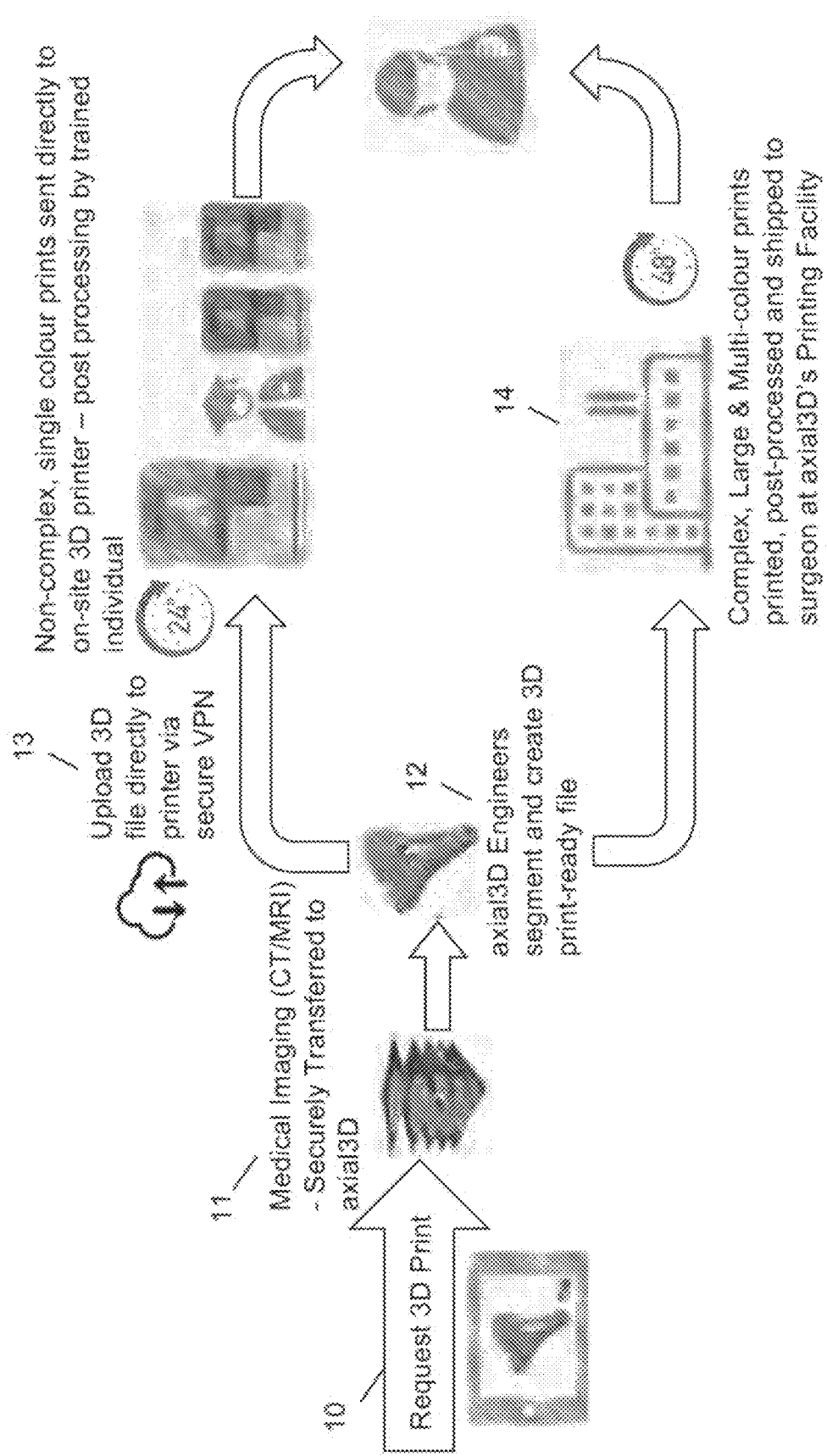
FIG. 1 shows a diagram illustrating the Axial3D system workflow.

FIG. 1 shows a diagram illustrating the Axial3D system workflow of ordering a 3D printed Model. The Axial3D system uses machine learning-based techniques to automatically produce patient-specific 3D anatomical models based on a patient's scans.

The 3D anatomical models may be generated, printed and delivered in 24-48 hours.

As shown in FIG. 1, a 3D print is requested via Axial3D dedicated portal as follows:

Register on the Axial3D ordering platform https://orders.axial3d.com/(10);

Select New print and complete patient details such as birth date, gender, anatomical region of interest, dispatch date, anatomical model service required, material type, pathology description, lead consultant details;

Send request to PACS manager or radiologist or upload DICOMS themselves (11);

3D annotation or written description is given of request Data is proceed by Axial3D software or personnel into a 3D printable file (12);

SLT/OBJ of final print ready file is sent securely via a VPN to a 3D printer on site with each printer having its own wireless (13);

3G/4G network that can send a receive data to Axial3D's web application;

If a print order is too large for internal capacity-Axial3D prints and sends a 3D model to customer.

If orders are too large or complex Axial3D prints are managed by Axial3D's printing service (14).

As an example, a clinician or radiologist may order a 3D print of a patient specific anatomic feature via the web portal. The Axial3D system then automates the entire steps of the 3D printing process from processing 2D medical images to sending instructions to a 3D printer for printing the patient specific anatomic feature. The clinician is then able to receive the 3D physical model in a timely manner, such as in 24 hours or 48 hours from placing the order, with minimum or zero involvement from his part. The Axial3D system also provides the clinician with an additional report of the specific anatomic feature alongside the 3D physical model based on a detailed analysis of the specific anatomic feature.

Cybersecurity Process in Medical 3D Printing

We have developed a digital platform to enable the secure and verifiable production and delivery of 3D printed anatomical models on demand and to deliver this globally, at scale and in a wide range of scenarios: making it available not just to health authorities, private hospitals and surgeries but ultimately any hospital. The technological challenge is to provide indisputable verification of the provenance of both the virtual model generated from a patient's anonymised data and any physical model that is 3D printed from it. The stakeholders involved in this process represent multiple parties spread across multiple organisations therefore they need to be reliably identified, authenticated and capable of independently verifying the provenance of these models.

This enables remote printing of 3D anatomical models, where the printing is done in one location and controlled remotely in another location. Once 3D physical models are ordered, 3D models are generated from 2D medical scans, and are then remotely reviewed, approved and controlled by a 3D printing technician.

The 3D printing technician may also control more than one printer remotely and the system is automatically able to decide how best to select or arrange the printing on the one or more printers.

The cybersecurity process is crucial in order to prove or validate that the printed 3D physical object is the one that was sent remotely and that it is associated with the correct patient without disclosing any patient confidential data.

Crypto Signing of Files

We create and store a hash of the 3D model file representing the 3D printable model of a specific anatomic feature and use that to recreate the object or 3D physical model anytime that it is required. This hash can be used to quickly establish if the file has been modified.

Every time we upload or make changes to the file on the web app we need to create a new hash however the one that is created at the end of the process is a canonical hash for the printed file. Therefore all previous files are quality controlled 'drafts'. The canonical is the file that we publish so that the user has the end file.

In the process of generating an anatomical model from medical scans the data undergoes a number of transformations and modifications. A hash file is generated at each of these steps in order to record these changes. The process of identifying anatomy in the scan produces labels on the scan that are subsequently used to generate a print file. The hashing process records this and acts as a history of the changes. Modifications to the file are stored and used to provide a trace of the provenance of the file. In this way the user can be assured of the providence of the file that they are using.

We have implemented a system that allows for the cryptographic signing of files and their subsequent distribution. The distribution of files for printing is managed by providing a decentralised file signing service. This is done by cryptographically signing the files using private/public key based encryption. This allows the verification of files by remote parties in a secure manner.

A service is provided that allows the download of the file and of any subsequent testing of the files for correctness. Files can be stored on object file system like S3 along with hash of file. A 'central' repository of hashes then links the file to the order. This repository may be a file, a database or a distributed ledger.

Figure 2:
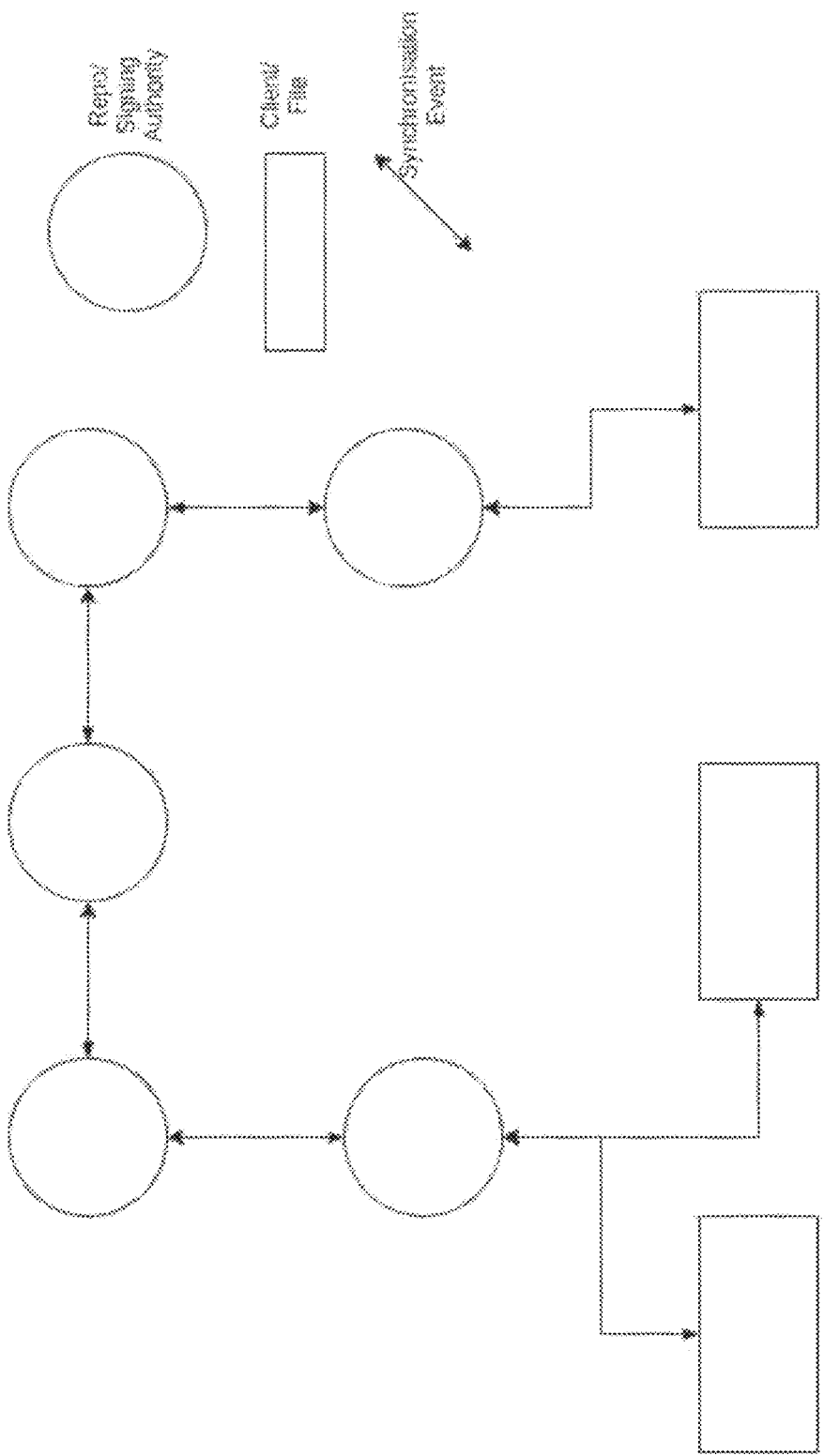
FIG. 2 shows a diagram illustrating hashing of the file of the 3D printable model.

FIG. 2 shows a diagram illustrating the tracking of modifications of the file, in which changes to a file are committed to the repository, and changes to an instance of the repository are synchronised between repositories.

Our system ensures that only validated files can be printed. Files are signed and only those that have passed the cryptographic challenge are accepted for printing. As a result only files that have been signed and verified against the verification server can be sent to the printer. This also means that all files can be encrypted both at rest and at transfer and that modifications can be recorded and observed without needing to see the contents of the file.

Our system may sit in front of printers ensuring that only encrypted files are sent for printing. Files can be decrypted in transit as the print is being completed and ensuring that only encrypted versions of the file are ever stored/transmitted.

Working Natively in 3D Space

Most segmentation methods work on applying algorithms to 2D images and 3D models are then generated from the segmented 2D images.

Figure 3:
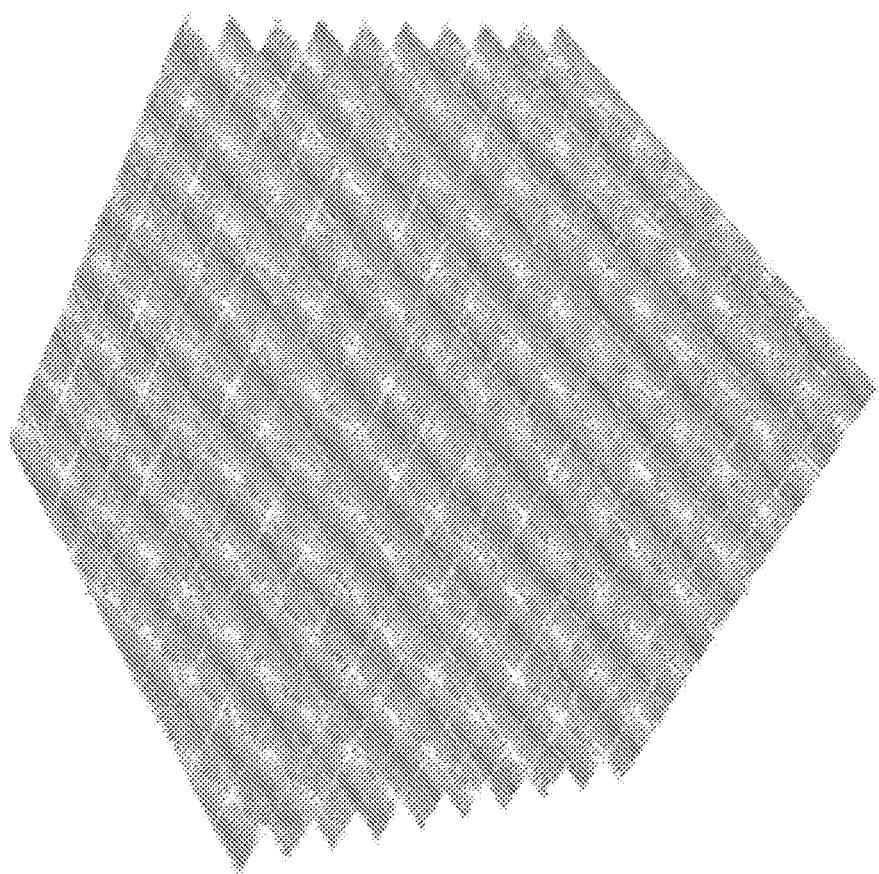
FIG. 3 shows a set of DICOM stack images with pixels indicated as boxes.
Figure 4:
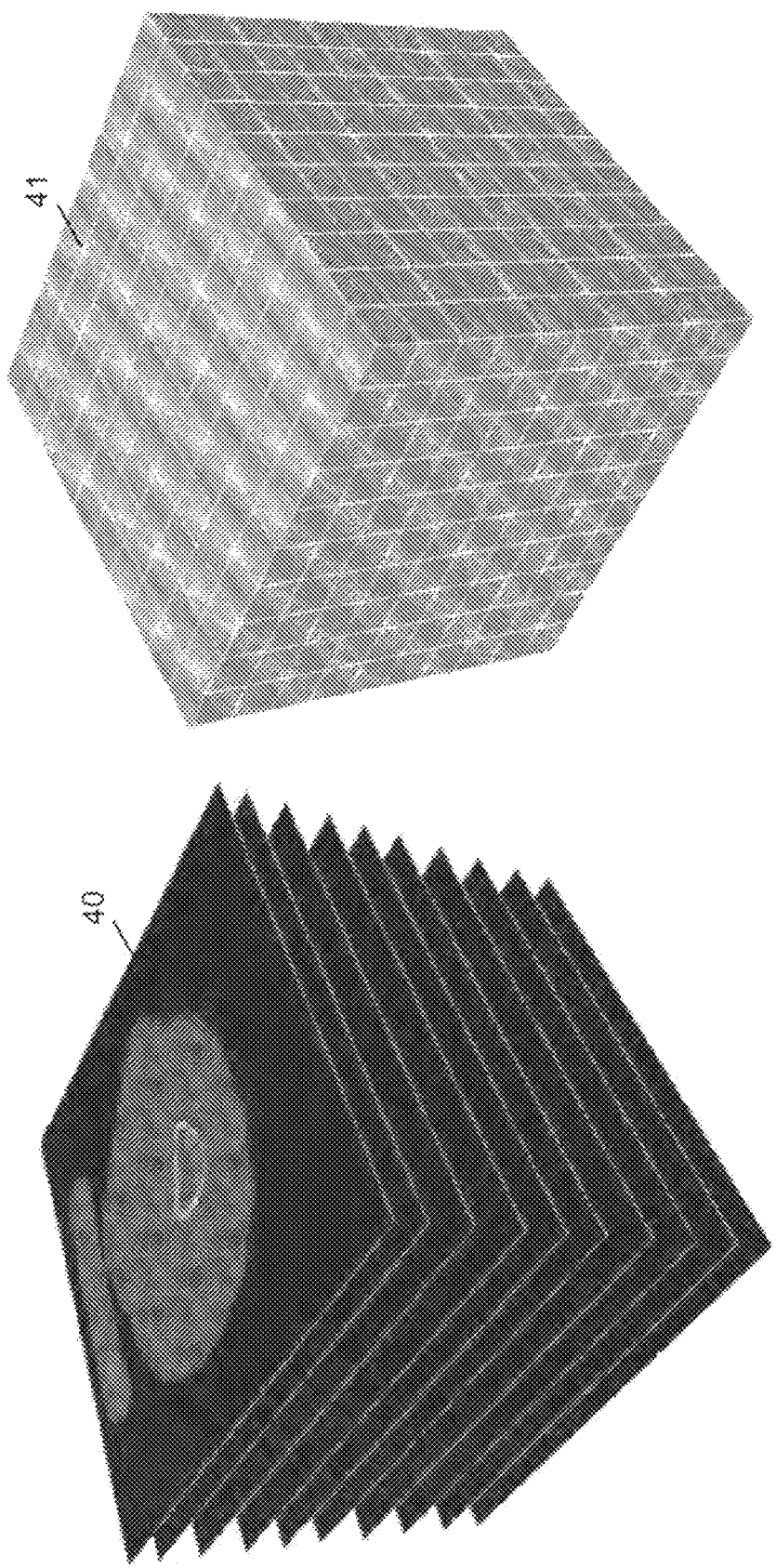
FIG. 4 shows a set of DICOM stack images and a 3D image with voxels indicated.

FIG. 3 shows a set of DICOM stack images with pixels indicated as boxes. FIG. 4 shows a set of DICOM stack images (40) and a 3D image with voxels indicated (41). We work natively in the 3D space by converting the scan slices shown in FIG. 3 into a single volume shown in FIG. 4. We compute the zero point of our coordinate system for the volume and orientate all slices in the scan to this. This allows us to calculate the alignment of slices with reference to the volume and observe properties of the set of slices. This means that we now natively work in 3D using 3D feature detection filters, essentially becoming a voxel classification rather than pixel based classifier.

Figure 5:
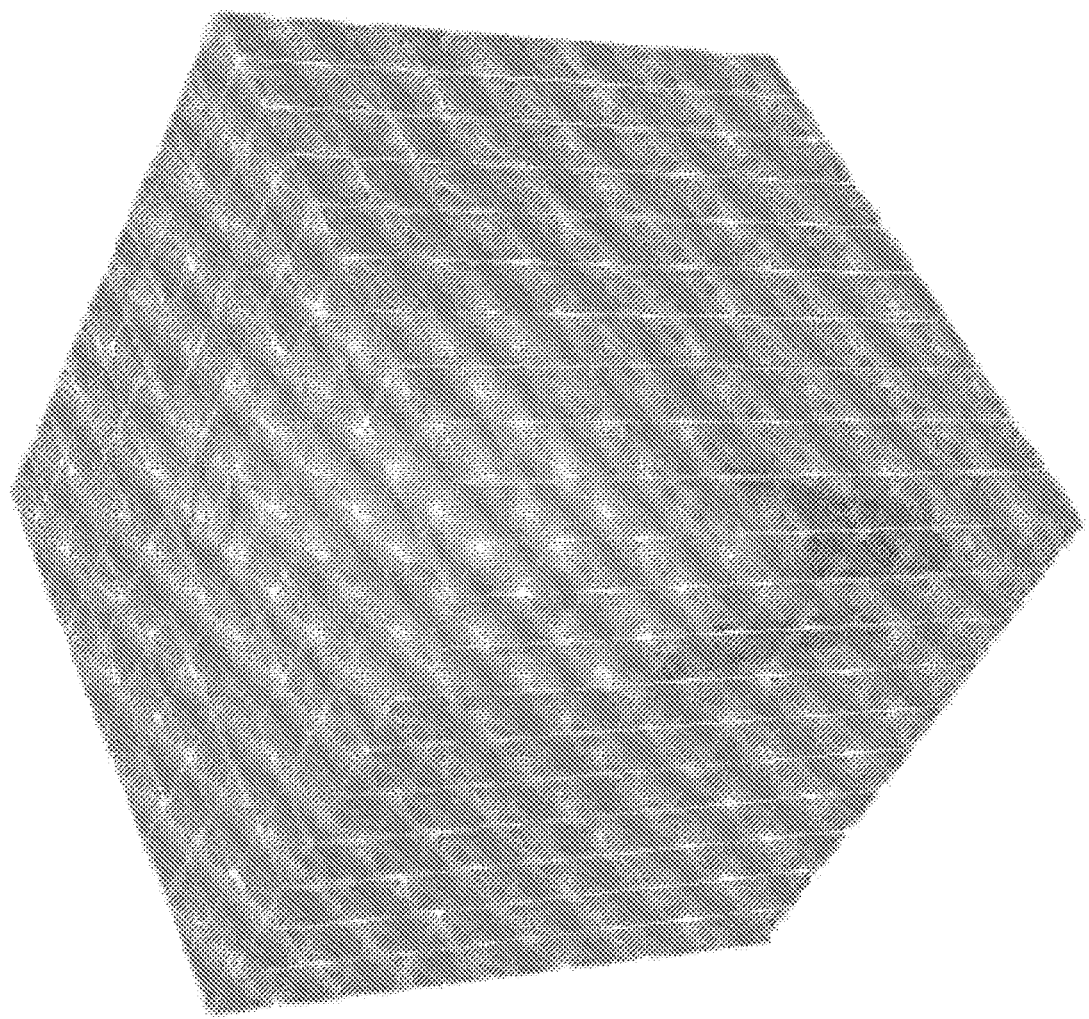
FIG. 5 shows a 3D image of making selections in the voxel space.
Figure 6:
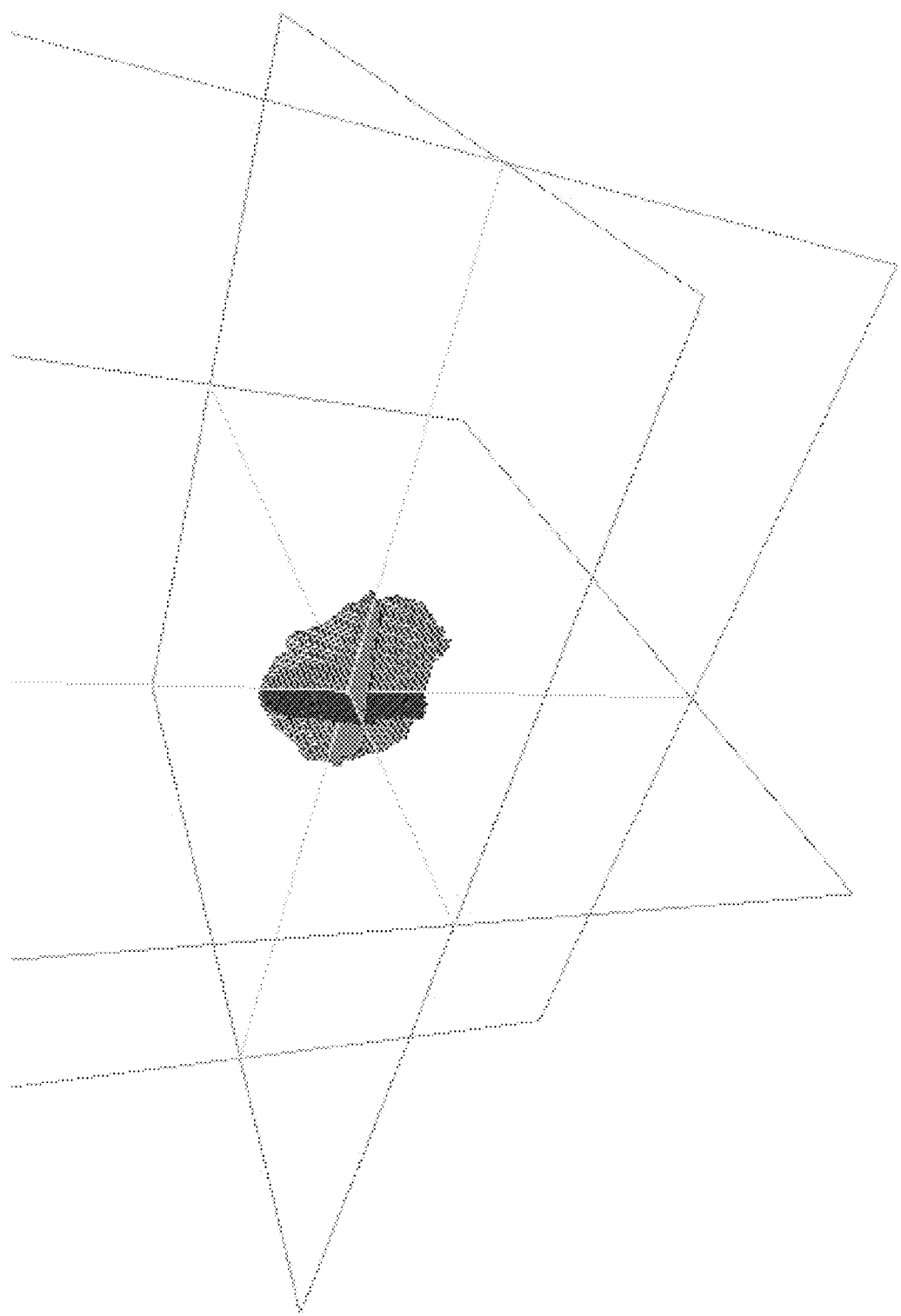
FIG. 6 shows a specific voxel from 3 orthogonal planes.

In FIG. 5 a knee is shown and specific voxels are highlighted. One key advantage of working natively in 3D is that the system incorporates orthogonal information in the scoring metric. This is most simply indicated by considering FIG. 6 where 3 planes are considered together. A particular voxel is shown with three planar cuts through that voxel which reveals more information about the likelihood of a voxel being a member of a specific class or not. By incorporating information from all planes for each voxel it is possible to identify junctions between bones or other sections of anatomy more effectively. This is because transitions in the image (e.g. voxel intensity) are easier to spot when considering all planes. The result is that all voxels in the scan can be used simultaneously to train the algorithm. In practice this means that larger, spatial and biological features can be encoded in the algorithm to overcome specific challenges at anatomical intersections such as myocardial wall to ventricle (heart) or bone joints such as those shown in FIG. 5.

Combining Image Registration and Making Multi Modal Inference

Figure 7:
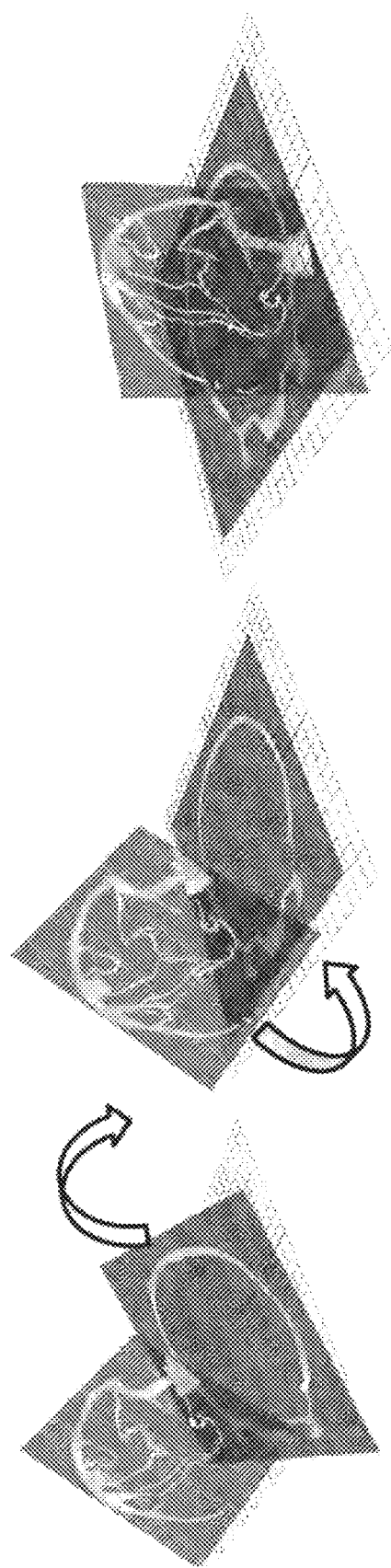
FIG. 7 shows data registration of two different datasets for a single patient.

We can register multiple image stacks and modalities (such as MRi & CT or Mri and Mri where different structures are highlighted in more detail) scans to overlay the voxels of the different scans as shown in FIG. 7 in which data registration of two different datasets for a single patient is illustrated. We can identify landmarks within the scans to facilitate mapping pixels from one scan to another. A landmark is a point or shape that is shared between individuals by common descent. It can be biologically meaningful such as the shape of the eye corner of the skull or mathematically expressed as the highest curvature point on a bone's surface. This means that information from the multiple scans can be used simultaneously to identify features for the machine learning algorithm. Since both modalities can be thought of as different views of the same anatomy the combination allows us to add additional information into the training phase. In this way 2D medical images, provided for example from CT, MRI, or PET scans, can be processed together.

The Axial3D system includes the steps of (i) receiving 2D medical images, (ii) automatically generating a 3D image from the 2D medical images, and (iii) processing the 3D image in order to segment or classify the 3D image. A 3D printable model can then be generated from the segmented 3D image.

The 3D image data file format includes for example any point cloud format or any other 3D imaging format.

Key features of the system are, but not limited to, the following:
Anatomical transitions are easier to identify since the 3D image includes image data from more than one direction. By comparison, information from only one direction is available when working with slices of 2D images.
Consequently, this also improves the identification of a specific anatomy.

Combining Information from Multiple Planes

In order to image a specific anatomy, cross-sectional images are taken at any angle. As an example, an MRI scan of the heart takes 2D images at different directions. Working natively in 3D improves the accuracy (as measured using standard metrics such as but not limited to the DICE coefficient) of the generated 3D printable model. On a per voxel basis the accuracy of the prediction is improved by considering the 3D properties of the voxel over considering the 2D properties of the pixels and combining them. Each plane or 2D image and it's constituent pixels become features of the 3D volume. For each voxel the features of each pixel are encoded as features of the voxel. The network is then trained and determines the appropriate weight to be given to each plane. Each feature is represented as a discrete range and is optimised by the neural network training process. In this way it is possible for the training process to learn the appropriate integration of the additional information from all planes.

Post Segmentation Utility of Anatomical Feature Delineation

When a piece of anatomy has been fully and accurately segmented it is possible to carry out measurement of a number of physical properties of the anatomy, for example the heart. The segmented anatomy can be measured by relating the pixel size to a physical scale from the coordinate system.

Parameters of the anatomic features are determined, such as, but not limited to:
The volume of the anatomical region;
The volume in a cavity of the anatomical feature e.g. the blood in each chamber of the heart;
The thickness of the different layers of the anatomical feature e.g. the heart wall;
The size and diameter of a feature, e.g. a blood vessel or bone;
The directional properties of a shape e.g. in scoliosis cases-detection of scoliosis and type of scoliosis, measuring or determining the angle or degree of curvature;
Cortical bone density-determination whether a screw is able to fit, or automatically determine the parameters of a screw that fits;
Aneurysm-will a coil or a clip fit be able to stop or block blood flow;
Force needed to break a bone;
Further information on the extent of a pathology or injury.
Information on an additional pathology that was not reported by the clinician, such as the location of a previously unknown fracture.

When a 3D printable model is ordered, the system produces and sends a report to the physician with the above information. This can improve a surgeon's preoperative planning, and further reduce costs to an healthcare provider. For example, from understanding vessel size more accurately, a surgeon may then make an informed choice for the right stent size prior to surgery. The system may also automatically determines the parameters of the stent.

Figure 8:
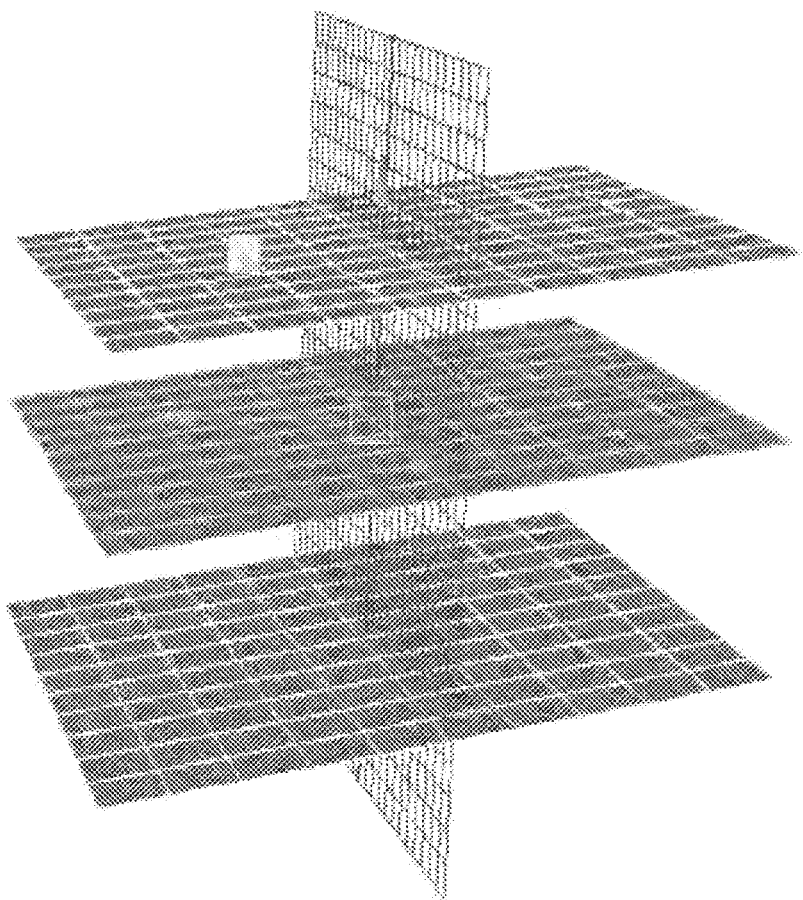
FIG. 8 shows a diagram illustrating equidistant slices in a particular plane.

Automatically Identify and Repair Spacial Errors and Inconsistencies in the Volumetric Data FIG. 8 shows a diagram illustrating equidistant slices in a particular plane. We are applying two methods one for identification of non equilinear slices and one for missing slices. The trajectory of the 2D slices is plotted and analysed. If a slice is found above or below a certain trajectory threshold, then it is removed from the analysis prior to the generation of the 3D image. The slices must be in planes that are congruent with respect to each other, they are occurring parallel and at an equal distance apart with respect to the base plane. Assuming that there exists a set of equilinear slices and we can identify such a set and such a set minus of the slices. We are therefore fault tolerant in the identification of equilinear slices to one.

Combining Interpolated Data from Multiple Slices Containing Slices from Multiple Angles.

We then have developed a method for inferring the missing data between two slices. This relies on the ability to create a missing slice with the correct 3D geometry and interpolated pixel values.

Many medical imaging datasets contain slices of the patient from multiple angles. While CT scanning is typically limited in its ability to obtain slices at standard angles, oblique scans are routinely acquired for MR scans. Oblique scans are often used in MR imaging in order to minimise the number of total images to be collected and therefore reduce the time and cost of performing a scan. Typically, when such technique is used, a relatively small number of slices is acquired at each oblique angle (typically 5 to 10 images) at large slice spacing (5 to 10 mm); the oblique scans are often taken at either three nearly perpendicular directions (axial, coronal, sagittal) plus an additional oblique axis, however, imaging angles and number of scans are to the discretion of the medical professional.

As a consequence, too few slices along a single axis may be provided to generate a complete volume of high enough quality. For example, the spacing between each slice may be greater than five millimetres, entirely missing important anatomical features.

Resulting images may only provide sufficient visual information on a specific lesion when viewed in combination: each portion of the lesion may be located in the large gaps of one of the scans, while it may be visible in the other ones. For example, a 10 mm tumor mass may be visible only in one slice of the axial scan, one of the coronal scans, and two slices of the sagittal scan; in this scenario, the oncologist will view the four images at the same time to obtain a 3 dimensional understanding of the tumor shape and volume.

The Axial3D system is able to automatically make decisions on how to process the 2D medical images in order to provide an accurate 3D physical print of a specific anatomic feature in which any critical or important features of the specific anatomic feature are made visible. These critical or important features may also be made readily accessible by splitting the 3D physical model into a set of connectable 3D physical models. These processing decisions may be based on the specific anatomic feature, a specific pathology or any other pre-configured or learnt parameter. This, in turn, aids in the diagnosis and treatment of patients, improving surgical planning and patient care.

In this method we show how to interpolate multiple simultaneous stacks into one volume. This leverages the intersecting slices to achieve higher information density and create a highly fidelity interpolation. The slice spacing for the reconstructed volume is limited by the original oblique scan spacing: depending on the number of oblique scans (typically 3 or four as mentioned above), the slice spacing of the reconstructed volume can be as low as a fifth of the original scan (eg if the oblique scans slice spacing varies between 5 and 6 mm, the reconstructed volume spacing can be as low as 1 mm).

The interpolation was achieved by finding the absolute positions of the corners of each DICOM image in each stack relative to origin determined by the scanner itself and reported in the DICOM header. This allowed a bounding box to be constructed to encompass all of the images in a space in which they are all embedded. By discretizing the bounding box so that it represented volume of voxels spanning the dimensions of all of the stacks, a mapping could be determined from the space of each stack of DICOMs to the new volume space. At each point in the new volume, the closest pixels K in the DICOMs to that point were determined and their distances d computed. The voxel value M at this point was then computed as the weighted sum:

$$M_{ijk} = \frac{\sum_\alpha K_\alpha q_\beta}{\sum_\beta q_\beta} \text{ where } q = d^{-1}$$

For each imaging orientation a stack of images was given as part of the original dataset and for each orientation there were 20-30 such stacks representing scans taken at those same locations but at different times. Each interpolation was generated for a series of DICOM images across all orientations of scan but for one time stamp.

This makes for a three dimensional interpolation. Hence, the original 2D slices from multiple angles are transformed into a set of evenly distributed parallel 2D slices prior to the generation of the 3D image.

Multi-Channel Training

Here we describe the addition of "above and below" slices alongside a typical input image to improve the segmentation network. This informs the neural network about continuous structures and those that are just spurious artefacts of a particular scan. We anticipate improvements in the neural network specifically at correctly identifying thinner bone filaments while simultaneously removing areas of an image that have similar Hounsfield values but aren't the same category of anatomy. For the three-channel example, the neural network would need to take inputs of the shape:

(batch_size, channels, X, Y)

The data is split in order to fit into the required memory size. The split data may then be fed into any neural network, or any image analysis platform.

Figure 9:
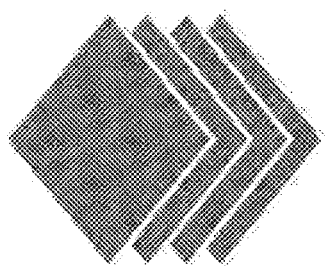
FIG. 9 shows a diagram illustrating the multi-channel training.
Figure 9:
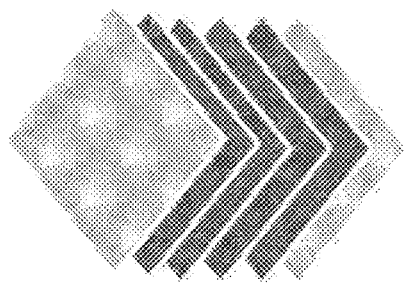
Figure 9:
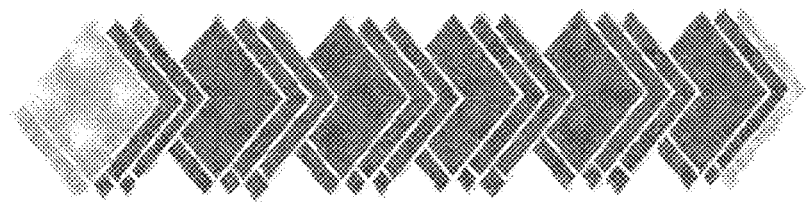

To achieve this, each stack was first padded with an 'image of zeros' on the top and bottom of the stack. This meant that groups of three slices could be formed into an object with the same total number of input objects, as shown in FIG. 9.

Figure 10:
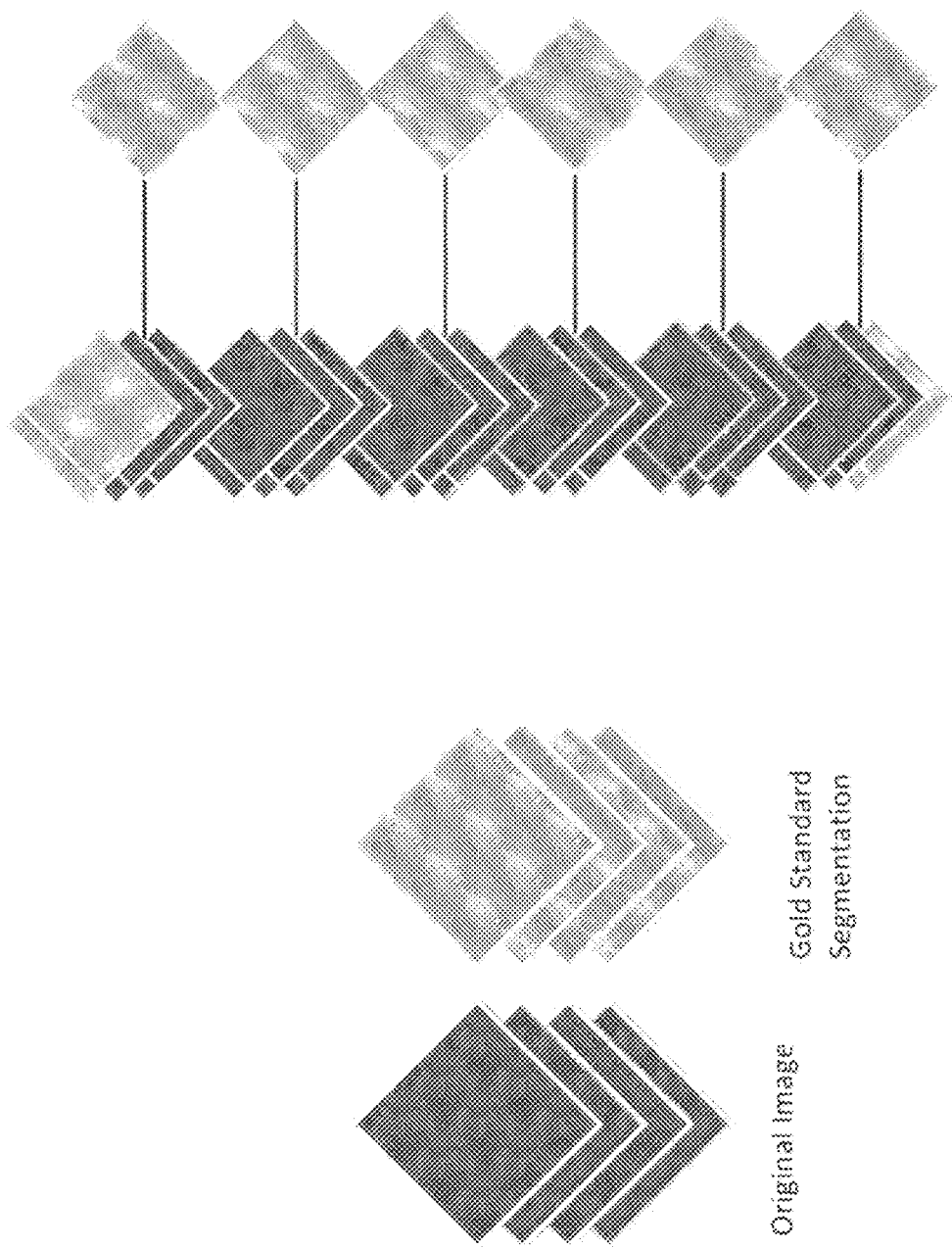
FIG. 10 shows a diagram illustrating the multi-channel training.

Each input triplet will have a ground truth or gold standard corresponding to the ground truth image associated with the central image, in order to give the "above and below" information, as shown in FIG. 10. Each image and ground truth pair will still exist when the extra channels have been added. The same principle applies for any number of odd channels; for every two more channels, another layer of padding should be added to retain the same number of inputs. The situation is slightly trickier when dealing with an even number of channels, but this is less desirable because it removes the nice aspect of symmetry. In practise, it might also be more useful to add a padding that corresponds to the minimum Hounsfield value of the stack, because this avoids a very strong transition which might hinder learning. In the case where an image has a padding image above or below it, there is simply less useful information to make a prediction with, the presence of the padding should not affect the prediction itself.

Examples of extracted 3D features are the following:
transition;
pixel intensity;
shapes;
3D shapes;

'Wireframe' Shape Detection

We generate the isosurface of the anatomical feature by transforming the probability distribution matrix from the inference algorithm into a discrete scalar volume. This is then used to generate a volumetric mesh that is a polygonal representation of the volume of the anatomical feature. After the surface is generated we draw a wireframe representation of the surface. This is composed a series of splines that form an outline of a given surface mesh. These can be compared to existing mesh outlines to see if they match.

Figure 11:
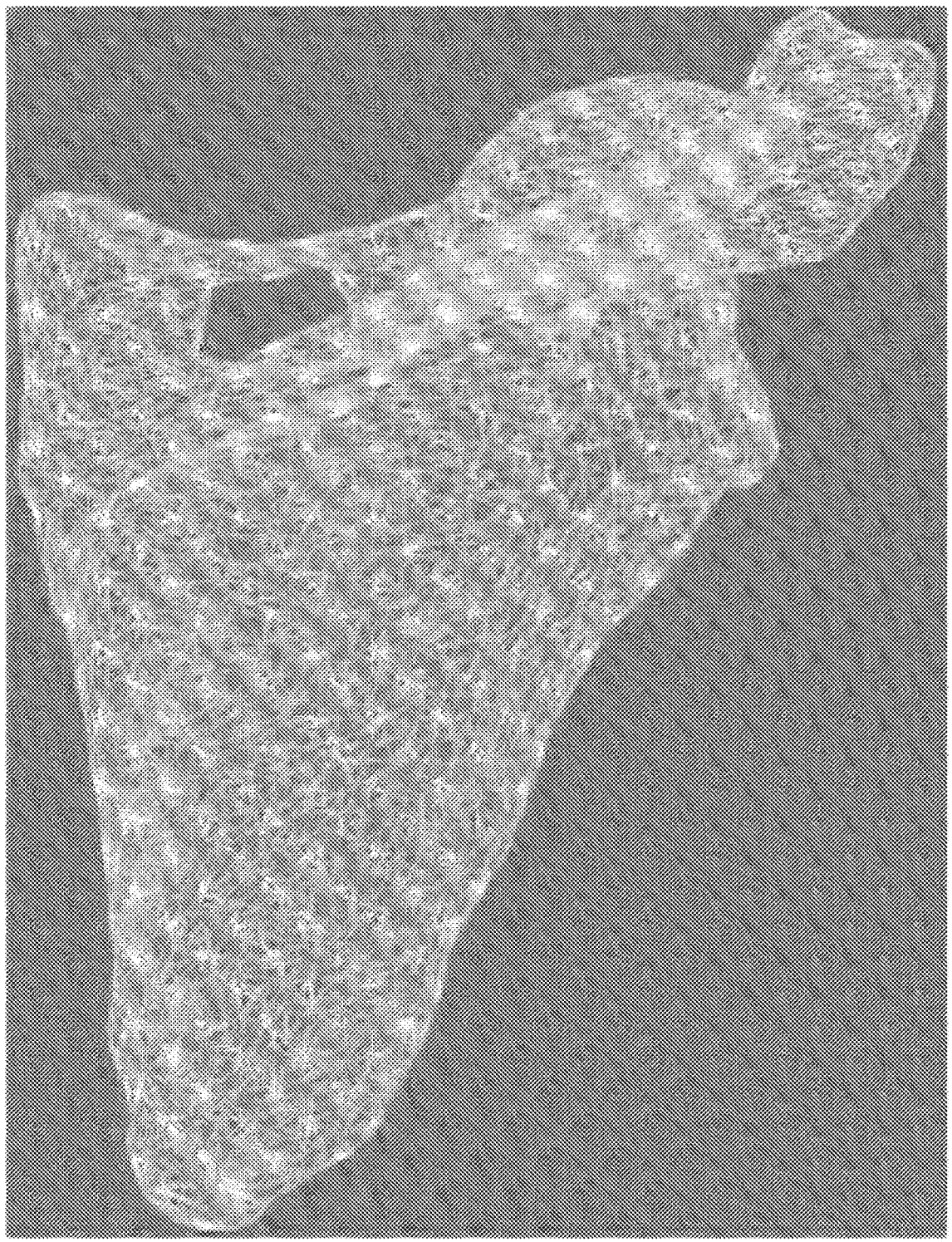
FIG. 11 shows a wireframe model of the mesh for a specific anatomy.

FIG. 11 shows a wireframe model of the mesh for a specific anatomy.

Figure 12:
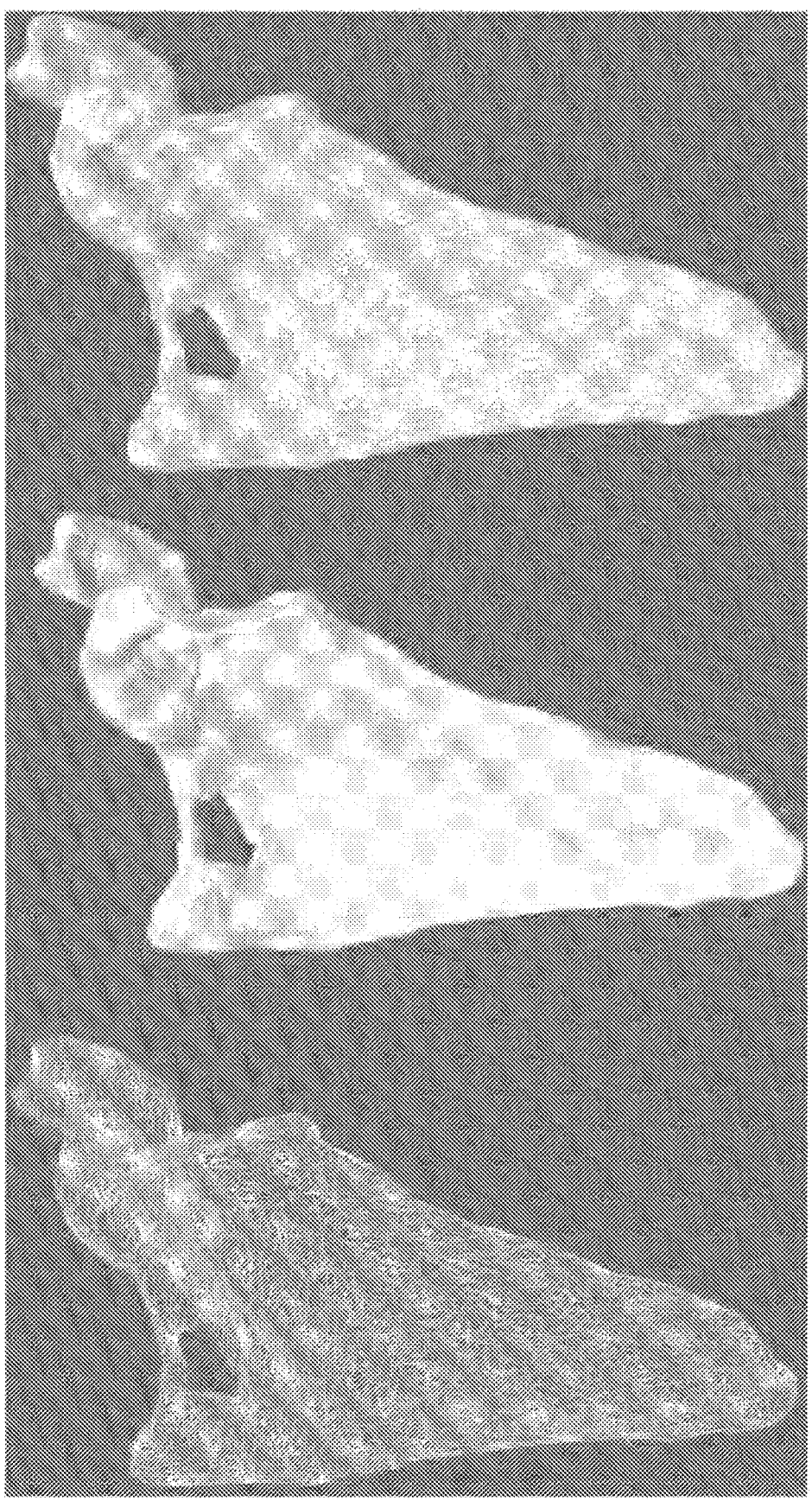
FIG. 12 shows diagrams of the wireframe model, the anatomy, and of an overlaid model of the anatomy with a verified wireframe model.

FIG. 12 shows diagrams of the wireframe model, the anatomy, and of an overlaid model of the anatomy with a verified wireframe model.

Building a wireframe model of the mesh helps to quickly identify a specific shape and its location in relation to the body. This, in turn improves the accuracy of the 3D printable model and of the 3D printed physical model.

Checking a line in one dimension to compare shapes is less computationally intensive than checking a 3D surface to compare shapes. In addition, checking for a continuous line helps in identifying continuous anatomy, whereas checking for a 3D surface is more prone to errors.

Simple method for determination of bone class. Lines can be drawn along the surface of anatomy that provide a unique identifier of the landmarks on the surface of the anatomy. ML models can be trained to identify sets of peaks and troughs in the surface line and relationships between them that allow for the classification of these surface lines and therefore the identification of anatomy.

Figure 13:
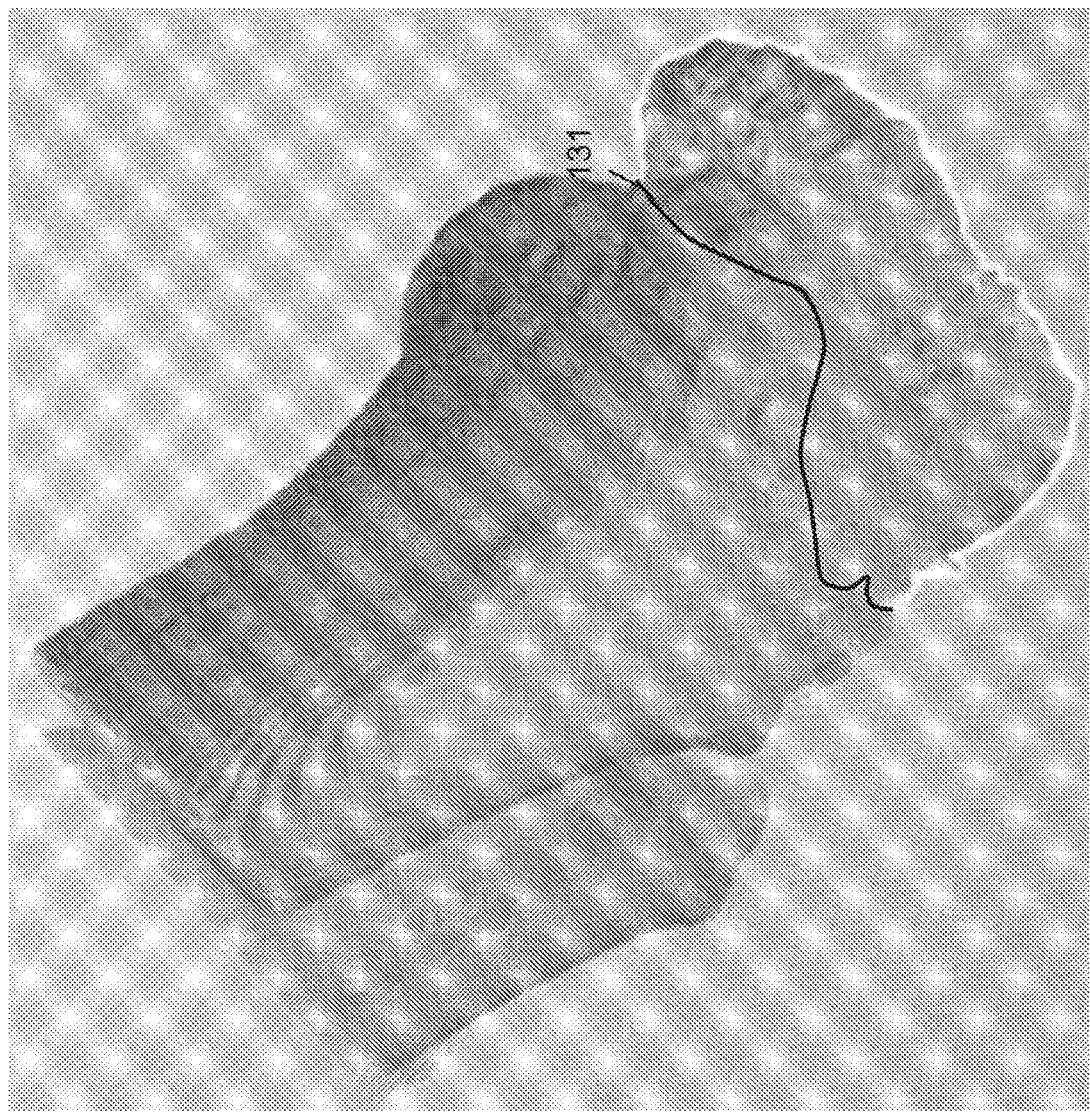
FIG. 13 shows a 3D bone model with a spline.

Wireframe representation of the mesh. It is possible to draw the single lines that form splines along the length of each bone in the scene, as shown in FIG. 13 where a line (131) from the wireframe model shows a spline of a bone.

Figure 14:
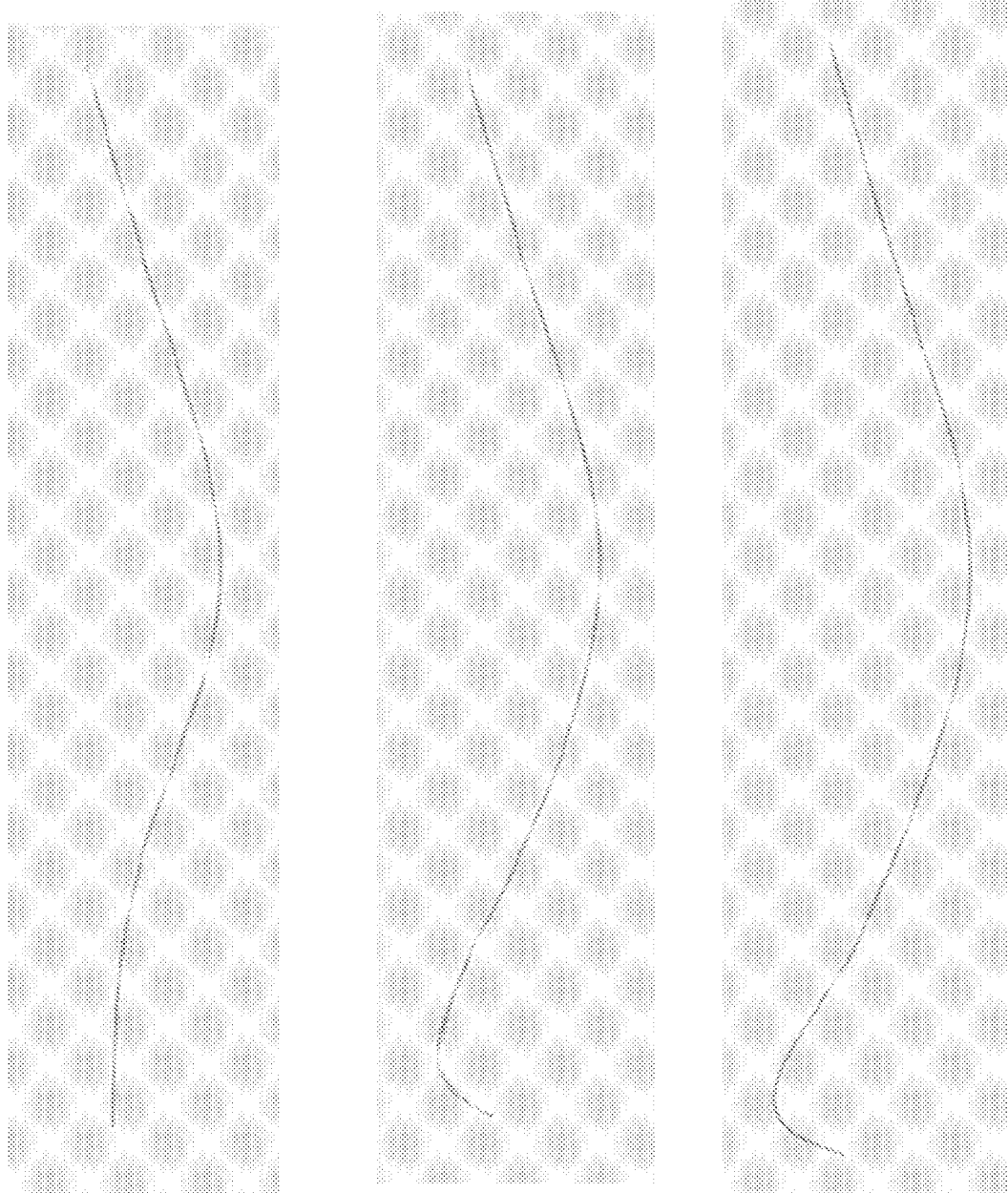
FIG. 14 shows three splines of a bone.

FIG. 14 shows a spline of a first bone, a spline of a second bone and a spline of a third bone.

The splines above show two different bones-spline 2 and 3 are the same bone in different people. A classifier can be trained to identify between the two splines. The classifier can include a PCA (Principle Component Analysis) classifier.

Orientation Fixing
Detecting overlap in shapes/volumes/meshes.
Allowing comparison between these shapes in 3D space.
Registration of images to the origin from DICOMs from two different scans (e.g. one MRI and one CT). This can be achieved in a number of ways; if the both sets of images make reference to the same origin point then it is possible to simply overlay the scans. However, if these are not present the algorithm will detect the anatomy in both scans and uses 3D object retrieval techniques to overlay the anatomy and recognise the same parts in the two scans. These can be combined with conventional technique from 2D registration to provide a higher level of confidence.

Auto Detect where to Place Dowels and Other Post Processing Steps

We carry out shape modeling whereby we determine the weakest and strongest position on the mesh. This can be achieved by bending and distorting the mesh and determining the points of maximum and minimum flex. The output of this stage will be a heatmap of the mesh, which provides a score of the strength of the mesh at a given point. This allows us to identify areas that require strengthening. It will also allow us to detect places that can be used for the placement of magnetic connections.

We have developed an algorithm that allows us to determine points of articulation in a 3D mesh. This is used by us to determine where the model should have additional support structures applied. We apply uniform vertical pressure on the mesh and identify the degree of rotation of the polygons upon application of pressure. Points or polygons that rotate by 90 degrees or more are in the most need of further reinforcement. Finite element analysis can be applied to the 3D mesh to develop a map of the mesh that captures structural properties of the mesh. This information can then be used to detect positions on the mesh that can be used to deploy dowels and other joining structures.

We have implemented heuristic algorithms that allow us to effectively enumerate the potential solutions to the problem and identify best fit solutions. We have defined criteria for the placement of dowels as support structures between parts of our models. We then use these as rules for optimisation of placement of such support structures. We employ wave functions to identify and optimise the placement of dowels and other structures in the 3D mesh. These are then solved by wave function collapsing which produces the optimal location of the dowel. Additional constraints can be placed on the solution that avoid particular features identified by the user.

Another use case is where we have split the model in two or more pieces and desire to reattach using magnets. We have developed an algorithm that allows us to identify the optimal location of these attaching magnets. This is an extension of the above algorithm whereby we add a further constraint on the torsion, squishing or twisting of the model that captures the property of the magnet.

Deconstructed Anatomy with Magnetic Connections

User defines split line through whole model or splits model through a non-uniform cut to separate specific pieces of anatomy (e.g. pubis and ilium from ischium within the hemi pelvis). The user then inputs diameter and depth of magnets and software automatically embeds magnet indents into surface of anatomy or if walls are too thin incorporates cylindrical inset on the exterior of model (embedded and cylindrical inset models below).

Parts are split such that it is not possible to connect the different parts together the wrong way. Magnetic or metal elements are placed to guide the different parts together. The metal elements are magnetically attracted to the element located to another part such that it is not possible to connect the different parts incorrectly.

Figure 15:
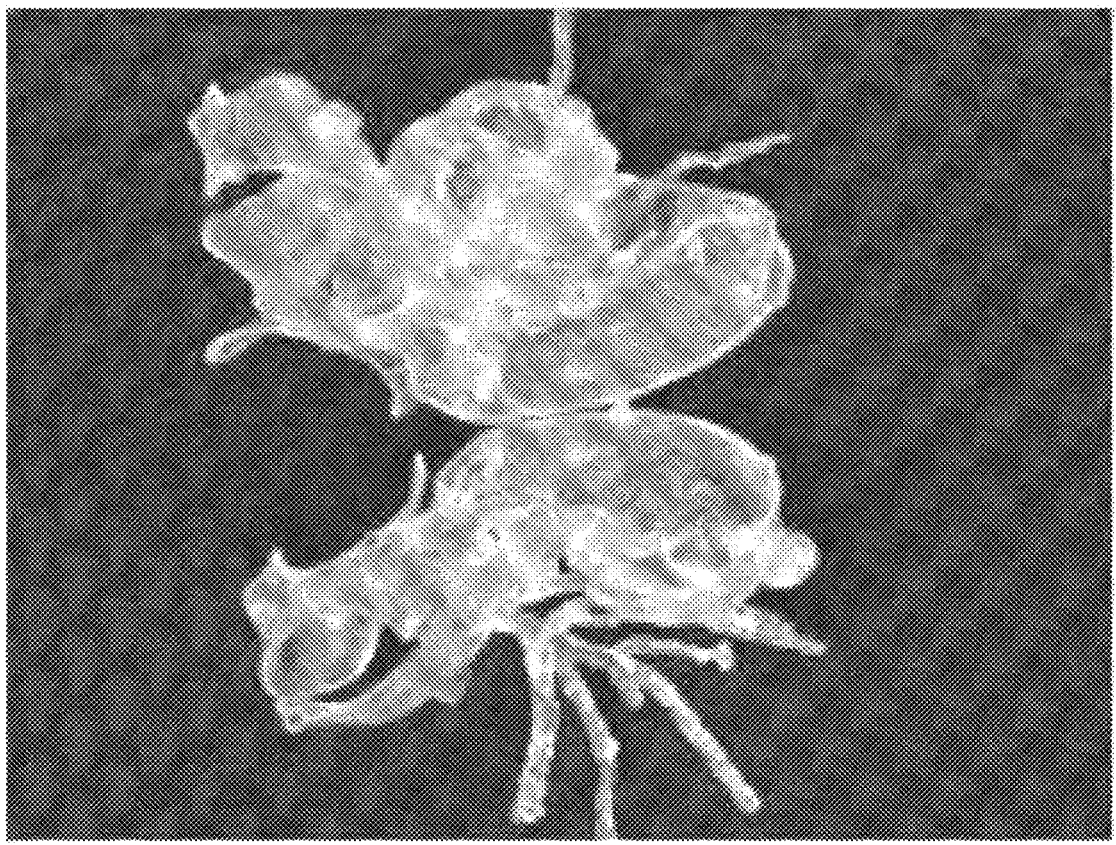
FIG. 15 shows a 3D printable model of a heart.
Figure 16:
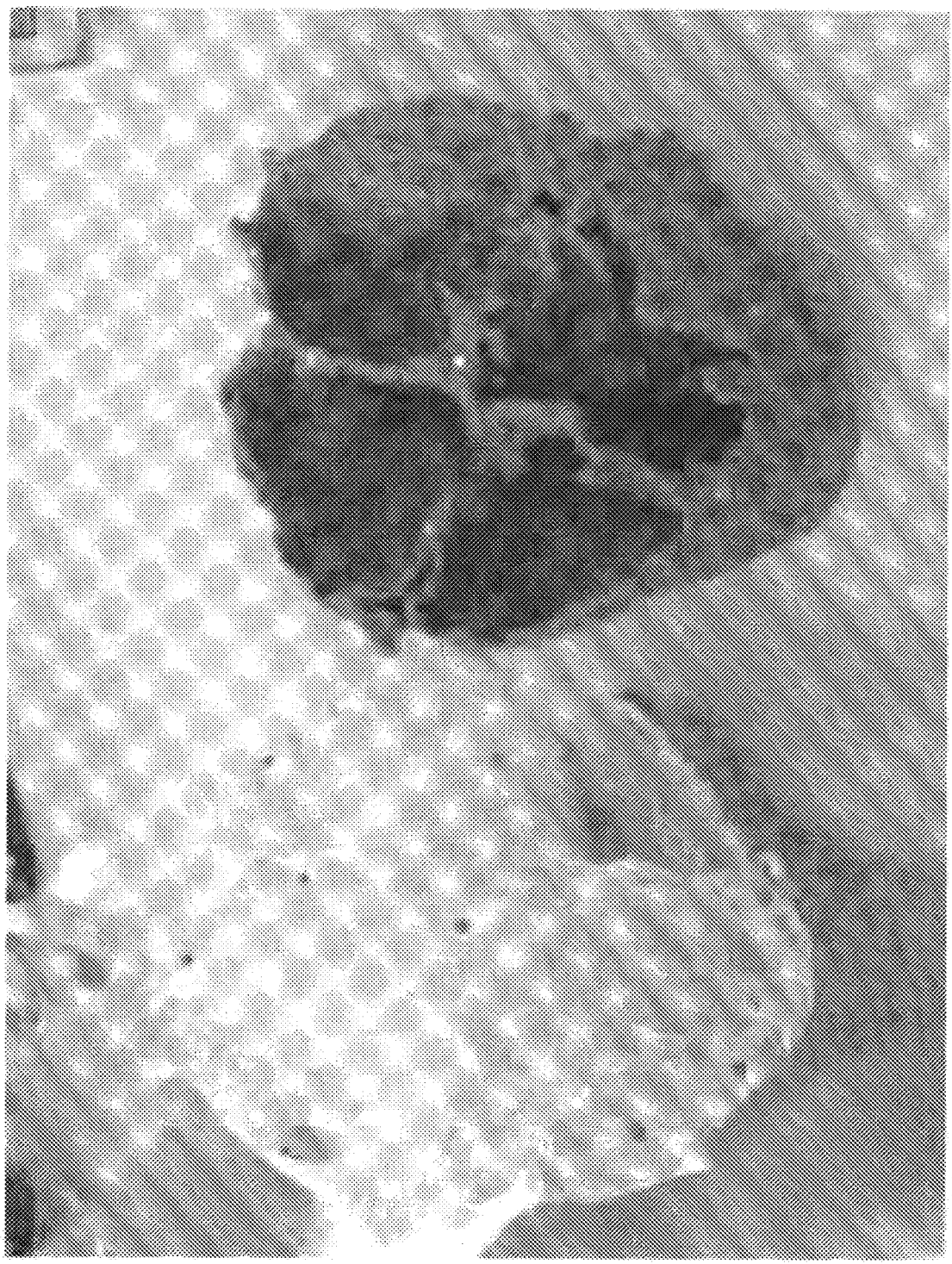
FIG. 16 shows a 3D physical model of a heart printed in two parts.

As an example, FIG. 15 shows a 3D printable model of the heart. FIG. 16 shows a 3D physical model of the heart printed in two separate parts. This enables a physician to view the 3D printed physical anatomy as a whole while at the same time being able to open it and see what is inside. The printed model can then be put together again knowing it has been put together in the correct way.

The different parts may be printed in different colors or with different material formulations i.e. soft and hard polymers.

Key Features

This section summarises the most important high-level features; an implementation of the invention may include one or more of these high-level features, or any combination of any of these. Note that each feature is therefore potentially a stand-alone invention and may be combined with any one or more other feature or features.

We Organise these Features into the Following Categories:
A. Working natively in 3D
B. Wireframe model
C. Splitting a 3D printable model into a set of 3D printable models
D. Remote printing A. Working Natively in 3D A computer implemented method for generating a 3D printable model of a patient specific anatomic feature from 2D medical images, in which:
(a) a 3D image is automatically generated from a set of 2D medical images;
(b) a machine learning based image segmentation technique is used to segment the generated 3D image; and
(c) a 3D printable model of the patient specific anatomic feature is created from the segmented 3D image.

Optional:
The set of 2D medical images are images from the patient taken from one or a combination of the following: CT, MRI, PET and/or SPCET scanner.

2D medical images from multiple scanning techniques are simultaneously processed.

The set of 2D medical images are automatically pre-processed such that important or critical features of the specific anatomic feature are made visible within the 3D printable model.

Pre-processing of the 2D medical images is based on the specific anatomic feature, specific pathology of the patient or any downstream application such as preoperative planning or training purpose.

Pre-processing of the 2D medical images is based on the specific anatomic feature or specific pathology of the patient.

The set of 2D medical images is pre-processed to generate a new set of 2D medical images which are evenly distributed according to a predetermined orientation.

The predetermined orientation is based on the patient specific anatomic feature, specific pathology of the patient or any downstream application such as preoperative planning or training purpose.

The predetermined orientation and spacing between each 2D medical image within the new set of 2D medical images are determined using machine learning techniques.

The predetermined orientation and spacing between each 2D medical image within the new set of 2D medical images are user configurable.

In which a missing slice from the set of 2D medical images is automatically detected.

A missing slice is corrected by generating an image corresponding to the missing slice using interpolation techniques.

The segmentation technique is based on one or a combination of the following techniques: threshold-based, decision tree, chained decision forest or a neural network method;

Voxel based classification technique is used in which voxel information from each axis or plane is taken into account.

The likelihood of a voxel of the 3D image having properties similar to the patient specific anatomic feature is calculated using a logistic or probabilistic function.

The neural network determines a weight for each axis or plane in a voxel of the 3D image.

Segmentation technique is further improved using multi-channel training.

In which each channel represents a 2D image corresponding to a slice position within the 3D space of the 3D image.

3D mesh model of the patient specific anatomic feature is generated from the segmented 3D image.

3D mesh model is further processed using finite element analysis.

points or areas in the 3D mesh model requiring further post processing steps are automatically detected.

Further post processing steps include placement of a dowel or other joining structure.

In which the optimal placement of a dowel or other joining structure is automatically determined.

3D printable model is based on the generated 3D mesh model.

The 3D printable model is 3D printed as a 3D physical model such that it represents a scale model of the patient specific anatomic feature such as a 1:1 scale model or a more appropriate scale model such as a reduced scale or enlarged scale model of the patient specific anatomic feature depending on the intended downstream application.

The 3D printable model is 3D printed with critical or important features of the specific anatomic feature made easily visible or accessible.

Parameters of the patient anatomic feature are determined from the generated 3D image, such as volume or dimensions of the anatomic feature, thicknesses of the different layers of the anatomic feature.

The specific anatomic feature is a heart and the measured parameters are: volume of the heart, volume of blood in each chamber of the heart, thickness of the different layers of the heart wall, size of a specific vessel.

B. Wireframe Model

Computer implemented method for identifying an anatomic feature from a set of 2D medical images, the method includes:

(a) generating a 3D mesh from the set of 2D medical images, in which the 3D mesh is a polygonal representation of the volume of the anatomic feature;

(b) extracting a line or spline from the 3D mesh along a direction of the anatomic feature; and (c) using a classifier to identify the anatomic feature from the extracted line or spline.

Optional:
The classifier is used to identify the physical properties of the anatomic feature from the extracted line or spline.

The classifier is used to identify a pathology of the anatomic feature from the extracted line or spline.

The method further includes the step of generating a wireframe model of the 3D mesh.

A 3D image is automatically generated from the set of 2D medical images and the 3D mesh is generated from the segmentation of the 3D image.

The classifier is trained to identify a specific anatomical feature.

The classifier is trained to determine parameters of the specific anatomic feature such as its location relative to the human body, dimension, thickness.

The classifier is trained to determine a potential defect or pathology of the specific anatomic feature.

The classifier is a principle component analysis classifier.

C. Splitting a 3D Printable Model into a Set of 3D Printable Models

Computer implemented method of splitting a 3D printable model of a patient specific anatomic feature into a set of 3D printable models, in which the method comprises the step of automatically splitting the 3D printable model into a set of 3D printable models, in which the 3D printable models include connective pieces, where the location of each connective piece has been automatically generated.

Optional:
Splitting of the 3D printable model is decided based on the patient's pathology and anatomy. Whereby, information cannot be gained from assessing the surface of the given structure alone.

Connective piece is a magnetic or metal element;

Each connective piece is located such that a set of 3D printed physical models from the set of 3D printable models can be connected to represent the patient specific anatomic feature and is prevented from being wrongfully connected.

The set of 3D printed physical models represent a scale model of the patient specific anatomic feature such as a 1:1 scale model or a more appropriate scale model such as a reduced scale or enlarged scale model of the patient specific anatomic feature depending on the intended downstream application.

critical or important features of the specific anatomic feature are made easily visible within the set of 3D printable physical models.

critical or important features of the specific anatomic feature are made easily accessible within the set of 3D printable physical models.

D. Remote Printing

A computer implemented method for printing a 3D model of a patient specific anatomic feature comprising:
- (a) uploading 2D medical images to a server,
- (b) processing at the server the 2D medical images into a 3D printable model of the patient specific anatomic feature; and
- (c) the server transmitting instructions for printing the 3D printable model to a printer, in which a security engine validates that the 3D printable model is associated with the correct patient data;

in which an end-user located at a remote location from the printer manages the printing of the 3D printable model.

Optional:

2D medical images and additional metadata are anonymised prior to being sent to the server such that no identifiable healthcare or personal information is transferred to the server.

The end-user remotely schedules, initiates or approves the printing of a 3D printable model on one or more printers via a Web application.

The end user remotely controls one or more printers and the printing is automatically arranged on the one or more printers.

A hash of a file corresponding to the file of the 3D printable model is created and stored within a central repository.

The central repository is accessed by the server, in which the central repository is a file, a database or a distributed ledger.

The hash is used to recreate or validate the printing or any subsequent printing of the 3D patient specific anatomic feature.

Modifications to the file are stored with the hash and used to provide an audit trail of the provenance of the file.

The hash is used to establish if a file has been modified.

the distribution of one or more files for 3D printing one or more specific anatomic features is managed by a centralized file signing service.

Files corresponding to the 3D printable model are encrypted using private/public key based encryption.

The security engine ensures only encrypted files are transmitted for printing.

Files are only decrypted in transit as a print is being completed.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

What is claimed:

1. A computer implemented method for generating a 3D image of a patient specific anatomic feature from 2D medical images, the method comprising:
   automatically pre-processing a set of 2D medical images to identify critical features of the patient specific anatomic feature based on a downstream preoperative planning application;
   automatically generating a 3D image from the pre-processed set of 2D medical images;
   using a machine learning based image segmentation technique to segment the generated 3D image;
   determining one or more parameters of the patient specific anatomic feature from the segmented 3D image; and
   automatically determining one or more structural parameters of a physical medical device selected for the downstream preoperative planning application based on the one or more parameters of the patient specific anatomic feature.

2. The method of claim 1, wherein the set of 2D medical images are images of a patient taken from one or a combination of the following: CT, MRI, PET and/or SPCET scanner.

3. The method of claim 1, wherein automatically pre-processing the set of 2D medical images comprises automatically pre-processing 2D medical images from multiple scanning techniques simultaneously.

4. The method of claim 3, further comprising identifying one or more landmarks within the 2D medical images to facilitate mapping pixels from one 2D medical image to another.

5. The method of claim 1, wherein automatically pre-processing the set of 2D medical images comprises automatically pre-processing the set of 2D medical images to generate a new set of 2D medical images which are evenly distributed according to a predetermined orientation based on the downstream preoperative planning application.

6. The method of claim 5, wherein the predetermined orientation and spacing between each 2D medical image within the new set of 2D medical images are determined using machine learning techniques.

7. The method of claim 1, wherein automatically pre-processing the set of 2D medical images to identify critical features of the patient specific anatomic feature comprises automatically pre-processing the set of 2D medical images to identify critical features of the patient specific anatomic feature based on a specific pathology.

8. The method of claim 7, further comprising receiving user input indicative of the specific pathology.

9. The method of claim 1, wherein automatically pre-processing the set of 2D medical images to identify critical features of the patient specific anatomic feature comprises automatically pre-processing the set of 2D medical images to identify critical features of the patient specific anatomic feature based on the patient specific anatomic feature.

10. The method of claim 1, wherein automatically pre-processing the set of 2D medical images to identify critical features of the patient specific anatomic feature comprises automatically pre-processing the set of 2D medical images to identify critical features of the patient specific anatomic feature based on a downstream training purpose application.

11. The method of claim 1, wherein the segmentation technique is based on one or a combination of the following techniques: threshold-based, decision tree, chained decision forest, and a neural network method.

12. The method of claim 1, wherein determining one or more parameters of the patient specific anatomic feature from the segmented 3D image comprises determining at least one of volume, dimensions, or thickness of different layers of the patient specific anatomic feature.

13. The method of claim 1, wherein the patient specific anatomic feature comprises a bone, and wherein automatically determining one or more structural parameters of the physical medical device selected for the downstream preoperative planning application comprises automatically determining one or more structural parameters of a screw based on one or more parameters of the bone.

14. The method of claim 13, wherein automatically determining one or more structural parameters of the screw based on one or more parameters of the bone comprises determining a size of the screw based on cortical bone density of the bone.

15. The method of claim 1, wherein the patient specific anatomic feature comprises a blood vessel, and wherein automatically determining one or more structural parameters of the physical medical device selected for the downstream preoperative planning application comprises automatically determining one or more structural parameters of a stent based on one or more parameters of the blood vessel.

16. The method of claim 15, wherein automatically determining one or more structural parameters of the stent based on one or more parameters of the blood vessel comprises determining a size of the stent based on a size of the blood vessel.

17. The method of claim 1, wherein automatically generating the 3D image from the pre-processed set of 2D medical images comprises automatically generating the 3D image from the pre-processed set of 2D medical images taken at a plurality of planes along a plurality of orientations to define a plurality of voxels, each voxel of the 3D image encoded with a feature of each pixel of the pre-processed set of 2D medical images associated with the respective voxel from each orientation of the plurality of orientations, the method further comprising:
using a neural network to determine a weight for each feature of each voxel associated with each orientation of the plurality of orientations,
wherein using the machine learning based image segmentation technique to segment the generated 3D image comprises using the machine learning based image segmentation technique to classify each voxel of the generated 3D image based at least in part on the determined weight of each feature of the respective voxel to segment the generated 3D image.

18. The method of claim 1, further comprising using a machine learning model to identify one or more landmarks on a surface of the patient specific anatomic feature.

19. The method of claim 18, wherein the machine learning model is trained to identify sets of peaks and troughs in surface lines drawn along the surface of the patient specific anatomic feature and relationships between them to classify the surface lines and identify the one or more landmarks.

20. The method of claim 1, further comprising:
creating a 3D printable model of the patient specific anatomic feature from the segmented 3D image,
wherein the critical features of the patient specific anatomic are visible within the 3D printable model.

21. The method of claim 20, wherein a 3D mesh model of the patient specific anatomic feature is generated from the segmented 3D image, and the 3D printable model is generated from the 3D mesh model.

22. The method of claim 20, further comprising 3D printing the 3D printable model as a 3D physical model.

23. The method of claim 1, further comprising automatically detecting a missing slice from the set of 2D medical images.

24. The method of claim 23, further comprising generating a 2D image corresponding to the missing slice using interpolation techniques.

25. A computer implemented system for generating a 3D image of a patient specific anatomic feature from 2D medical images, the system comprising a processor configured to:
automatically pre-process a set of 2D medical images to identify critical features of the patient specific anatomic feature based on a downstream preoperative planning application;
automatically generate a 3D image from the pre-processed set of 2D medical images;
use a machine learning based image segmentation technique to segment the generated 3D image;
determine one or more parameters of the patient specific anatomic feature from the segmented 3D image; and
automatically determine one or more structural parameters of a physical medical device selected for the downstream preoperative planning application based on the one or more parameters of the patient specific anatomic feature.

26. The system of claim 25, where the processor is configured to:
automatically pre-process 2D medical images from multiple scanning techniques simultaneously; and
identify one or more landmarks within the 2D medical images to facilitate mapping pixels from one 2D medical image to another.

27. The system of claim 25, where the processor is configured to:
automatically pre-process the set of 2D medical images to identify critical features of the patient specific anatomic feature based on a specific pathology.

28. The system of claim 25, wherein the patient specific anatomic feature comprises a bone, and wherein the processor is configured to automatically determine one or more structural parameters of a screw based on one or more parameters of the bone.

29. The system of claim 25, wherein the patient specific anatomic feature comprises a blood vessel, and wherein the processor is configured to automatically determine one or more structural parameters of a stent based on one or more parameters of the blood vessel.

30. The system of claim 25, wherein the processor is configured to use a machine learning model to identify one or more landmarks on a surface of the patient specific anatomic feature.

* * * * *